US011077032B2

(12) United States Patent
Goutayer et al.

(10) Patent No.: US 11,077,032 B2
(45) Date of Patent: Aug. 3, 2021

(54) STABLE DISPERSIONS CONTAINING DROPS COMPRISING A GELLING AGENT

(71) Applicant: CAPSUM, Marseilles (FR)

(72) Inventors: Mathieu Goutayer, Saint Malo (FR); Amélie Pujol, Marseilles (FR)

(73) Assignee: CAPSUM, Marseilles (FR)

( * ) Notice: Subject to any disclaimer, the term of this patent is extended or adjusted under 35 U.S.C. 154(b) by 90 days.

(21) Appl. No.: 15/760,961

(22) PCT Filed: Sep. 16, 2016

(86) PCT No.: PCT/EP2016/071934
§ 371 (c)(1),
(2) Date: Jul. 6, 2018

(87) PCT Pub. No.: WO2017/046305
PCT Pub. Date: Mar. 23, 2017

(65) Prior Publication Data
US 2019/0060186 A1 Feb. 28, 2019

(30) Foreign Application Priority Data
Sep. 18, 2015 (FR) ...................................... 1558850

(51) Int. Cl.
| | | |
|---|---|---|
| *A61K 8/11* | (2006.01) | |
| *A61Q 19/00* | (2006.01) | |
| *A61Q 19/08* | (2006.01) | |
| *A61Q 13/00* | (2006.01) | |
| *A61Q 1/02* | (2006.01) | |
| *A61K 8/04* | (2006.01) | |
| *A61K 8/34* | (2006.01) | |
| *A61K 8/73* | (2006.01) | |
| *A61K 8/898* | (2006.01) | |
| *A61K 8/37* | (2006.01) | |
| *A61K 8/19* | (2006.01) | |
| *A61K 8/81* | (2006.01) | |
| *B01J 13/00* | (2006.01) | |
| *B01J 13/10* | (2006.01) | |

(52) U.S. Cl.
CPC ............... *A61K 8/11* (2013.01); *A61K 8/042* (2013.01); *A61K 8/044* (2013.01); *A61K 8/19* (2013.01); *A61K 8/345* (2013.01); *A61K 8/37* (2013.01); *A61K 8/732* (2013.01); *A61K 8/8147* (2013.01); *A61K 8/898* (2013.01); *A61Q 1/02* (2013.01); *A61Q 13/00* (2013.01); *A61Q 19/00* (2013.01); *A61Q 19/08* (2013.01); *B01J 13/0052* (2013.01); *B01J 13/0065* (2013.01); *B01J 13/10* (2013.01); *A61K 2800/412* (2013.01); *A61K 2800/5424* (2013.01); *A61K 2800/5426* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 5,783,657 A | 7/1998 | Pavlin | |
| 5,874,069 A | 2/1999 | Mendolia | |
| 5,919,441 A | 7/1999 | Mendolia | |
| 5,981,680 A | 11/1999 | Petroff | |
| 6,051,216 A | 4/2000 | Barr | |
| 9,023,328 B2 | 5/2015 | Dumousseaux et al. | |
| 9,277,759 B2 | 3/2016 | Bibette et al. | |
| 10,300,006 B2 * | 5/2019 | Goutayer ............. | A23D 7/0053 |
| 2006/0141046 A1 | 7/2006 | Cattaneo | |
| 2014/0045949 A1 * | 2/2014 | Goutayer ............. | A23D 7/0053 514/772.6 |
| 2016/0262990 A1 | 9/2016 | Goutayer et al. | |

FOREIGN PATENT DOCUMENTS

| | | | | |
|---|---|---|---|---|
| EP | 1386600 A1 * | 2/2004 | ............. | A61K 8/732 |
| EP | 1 808 479 A1 | 7/2007 | | |
| EP | 2 353 577 A2 | 8/2011 | | |
| FR | 2 972 367 A1 | 9/2012 | | |
| FR | 2 976 824 A1 | 12/2012 | | |
| JP | H02-295912 A | 12/1990 | | |
| WO | 02/47619 A2 | 6/2002 | | |
| WO | 02/056847 A1 | 7/2002 | | |
| WO | 2010/063937 A1 | 6/2010 | | |
| WO | 2012/120043 A2 | 9/2012 | | |
| WO | 2015/044084 A1 | 4/2015 | | |
| WO | 2015/055748 A1 | 4/2015 | | |
| WO | 2015/148892 A1 | 10/2015 | | |

OTHER PUBLICATIONS

International Search Report dated Oct. 26, 2016 for the related International Application No. PCT/EP2016/071934.

* cited by examiner

*Primary Examiner* — Dominic Lazaro
(74) *Attorney, Agent, or Firm* — Pearne & Gordon LLP

(57) ABSTRACT

A dispersion containing a dispersed phase comprising drops and a continuous aqueous phase, preferably in the form of a gel, in which the drops comprise a fatty phase containing at least one gelling agent and a shell, wherein the shell comprises at least one anionic polymer and at least one cationic polymer.

19 Claims, No Drawings

STABLE DISPERSIONS CONTAINING DROPS COMPRISING A GELLING AGENT

CROSS-REFERENCE TO RELATED APPLICATIONS

This application is a National Stage application of PCT international application PCT/EP2016/071924, filed on Sep. 16, 2016 which claims the priority of French Patent Application No. 15 58847, filed on Sep. 18, 2015, both of which are incorporated herein by reference in their entirety.

The present invention relates to stable dispersions containing drops comprising a gelling agent, as well as their uses in the cosmetic field.

To date, there are dispersions of drops of a fatty phase dispersed in an aqueous phase, in particular as described in applications WO 2012/120043, FR 2 972 367 and FR 2 976 824. These dispersions are obtained, in particular by using a microfluidic method.

Dispersions of this type generally have low mechanical strength, which may lead to shearing or fragmentation of the drops during the transport of dispersions or cosmetic products containing them. It is also known that dispersions of this type, when they are obtained by means of a microfluidic method, may only be marketed in packaging requiring a specific atmosphere that is free of air (so-called "airless packaging"), which restricts their use.

There is, therefore, a need for new dispersions that are stable and have significant mechanical strength.

Moreover, the simplification of the method for preparing such dispersions remains a constant objective.

The object of the present invention is to provide a stable dispersion of drops dispersed in a continuous aqueous phase.

Another object of the invention is to provide a dispersion of drops dispersed in a continuous aqueous phase and having viscosities compatible with easy handling of the product obtained.

Another object of the invention is to provide a dispersion of drops dispersed in a continuous aqueous phase and having high mechanical strength, allowing it, in particular, to resist shearing or fragmentation of the drops during the transport of the dispersion or cosmetic products containing it.

Another object of the invention is to provide a simplified method for the preparation of the dispersions.

Thus, the present invention relates to a dispersion containing a dispersed phase comprising drops and a continuous aqueous phase, preferably in the form of a gel, in which the drops comprise a fatty phase containing at least one gelling agent and a shell, wherein the shell comprises at least one anionic polymer and at least one cationic polymer.

In the context of the present invention, the abovementioned dispersions may be denoted by the term "emulsions".

A drop according to the invention is composed of a core, also called the interior of the drop, surrounded by a shell, which isolates the inside of the drop from the continuous phase of the emulsion.

According to one embodiment, the dispersions according to the invention do not comprise any surfactant. They are therefore different from the usual cosmetic dispersions.

The dispersions according to the invention are of particular interest as regards the texture by being different from "conventional" emulsions stabilized by surfactants. In fact, the dispersions according to the invention are characterized by a unique, light and voluble texture, providing a two-stage application. More particularly, the dispersions according to the invention, or even the compositions comprising them, spread easily on the skin. The first moments of application are very aqueous with a marked brittle effect. Then, the feeling evolves towards an oily veil that fades away to leave a light and hydrated skin.

This texture is particularly advantageous and surprising to those skilled in the art in view of the absence of surfactants in these emulsions.

Moreover, the dispersions according to the invention are of interest as regards the texture and the sensory effect by being different from the dispersions described in WO/2012/120043. More particularly, the application to a keratin material, in particular the skin, of a dispersion according to the invention leads, at the moment of its spreading, to shearing of the gelled drops. Thus, the sensory effect provided by this application results in a feeling of the gelled drops literally melting under the effect of spreading and an enhanced oily effect.

The present invention also relates to the use of at least one fatty phase gelling agent to improve the mechanical strength of the drops of a dispersion according to the invention.

According to the invention, the pH of the dispersion is typically from 5.0 to 7.0.

According to one embodiment, a dispersion according to the invention is prepared by implementing a "non-microfluidic" method, i.e. by simple emulsification, for the preparation of a dispersion according to the invention, wherein the size of the drops of the dispersed phase is less than 500 µm, or even less than 200 µm. Preferably, the size of the drops is between 0.5 µm and 50 µm, preferably between 1 µm and 20 µm.

According to this embodiment, the present invention thus makes it possible to have drops of reduced size, in particular compared with drops obtained by a microfluidic method. This small size of drops will have an effect on the texture. In fact, a composition according to the invention and that is formed of finely dispersed drops, offers improved lubricity qualities.

According to another embodiment, a dispersion according to the invention is prepared by implementing a "microfluidic" method, in particular as described below. According to this embodiment, the droplet size of the dispersed phase is greater than 500 µm, or even greater than 1000 µm. Preferably, according to this embodiment, the size of the drops is between 500 and 3000 µm, preferably between 1000 µm and 2000 µm.

As such, it was not obvious that the emulsions comprising such drops of size greater than 500 µm should be stable.

This interesting property in terms of kinetic stability is all the more unexpected, as the shell of the drops, described in detail below, is very fine. Thus, at the time of application to a keratin material, no resistance related to the breaking of the shell is felt by the user, while no residual deposit of the shell is otherwise noted. This is referred to as an evanescent shell.

The drops of a dispersion according to the invention, by the nature and the properties of their shells, therefore differ from solid capsules, i.e. capsules provided with a solid membrane, such as, for example, those described in WO 2010/063937.

In the context of the present invention, the term "size" refers to the diameter, in particular the average diameter, of the drops.

Viscosity

The viscosity of the dispersions according to the invention, or even compositions comprising them, may vary considerably, which thus makes it possible to obtain varied textures.

According to one embodiment, a dispersion according to the invention has a viscosity of from 1 mPa·s to 500,000 mPa·s, preferably from 10 mPa·s to 300,000 mPa·s, more preferably from 400 mPa·s to 100,000 mPa·s, and most preferably from 1000 mPa·s to 30,000 mPa·s, as measured at 25° C.

The viscosity is measured at ambient temperature, for example T=25° C.±2° C. and at ambient pressure, for example 1013 mbar, by the following method.

A Brookfield type viscometer, typically a Brookfield RVDV-E digital viscometer (spring twist torque of 7187.0 dyne-cm), is used, wherein this is a rotational speed viscometer equipped with a spindle. A rotational speed is imposed on the spindle and the measurement of the torque exerted on the spindle makes it possible to determine the viscosity by knowing the geometry/shape parameters of the spindle used.

For example, a spindle of size No. 04 (Brookfield reference: RV4) may be used. The shear rate corresponding to the measurement of the viscosity is defined by the spindle used and the speed of rotation thereof.

The viscosity measurement is carried out for 1 minute at ambient temperature (T=25° C.±2° C.). About 150 g of solution are placed in a beaker of 250 ml volume and having a diameter of about 7 cm, so that the height of the volume occupied by the 150 g of solution is sufficient to reach the reference marked on the spindle. Then, the viscometer is started at a speed of 10 rpm and one waits until the value displayed on the screen is stable. This measurement gives the viscosity of the tested fluid, as mentioned in the context of the present invention.

Continuous Aqueous Phase

As indicated above, the dispersions according to the invention comprise a continuous aqueous phase, preferably in the form of a gel, in particular a gel having a viscosity that is designed to suspend the drops and thus contribute to the attractive and novel visual effect of a dispersion according to the invention.

According to one embodiment, the aqueous phase has a viscosity of between 400 mPa·s and 100,000 mPa·s, preferably between 800 mPa·s and 30,000 mPa·s, as measured at 25° C.

This viscosity is measured according to the method described above.

The continuous phase of the dispersions comprises water.

In addition to distilled or deionized water, water suitable for the invention may also be natural spring water or floral water.

According to one embodiment, the mass percentage of water of the aqueous continuous phase is at least 30%, preferably at least 40%, more preferably at least 50%, and particularly preferably at least 60%, in particular preferably between 70% and 98%, and most preferably between 75% and 95%, relative to the total mass of the continuous phase.

The continuous aqueous phase of the dispersion according to the invention may further comprise at least one base. It may comprise a single base or a mixture of several different bases. The presence of at least one base in the aqueous continuous phase contributes, in particular, to enhancing the viscosity of the latter.

According to one embodiment, the base present in the aqueous phase is a mineral base.

According to one embodiment, the mineral base is selected from the group consisting of alkali metal hydroxides and alkaline earth metal hydroxides.

Preferably, the mineral base is an alkali metal hydroxide, and especially NaOH.

According to one embodiment, the base present in the aqueous phase is an organic base. Among organic bases, mention may be made, for example, of ammonia, pyridine, triethanolamine, aminomethyl-propanol, or else triethylamine.

A dispersion according to the invention may comprise from 0.01% to 10% by weight, preferably from 0.01% to 5% by weight, and more preferably from 0.02% to 1% by weight of base, preferably a mineral base, and especially NaOH, relative to the total weight of the dispersion.

According to one embodiment, the dispersions according to the invention do not comprise a surfactant.

According to another embodiment, the aqueous continuous phase may further comprise at least one surfactant.

The surfactant is preferably an anionic surfactant, a nonionic surfactant, a cationic surfactant, or a mixture thereof. The molecular weight of the surfactant is between 150 g/mol and 10,000 g/mol, advantageously between 250 g/mol and 1500 g/mol.

In the case where the surfactant is an anionic surfactant, it is, for example, chosen from alkyl sulphates, alkyl sulphonates, alkyl aryl sulphonates, alkaline alkyl phosphates, dialkyl sulphosuccinates, alkaline earth salts of saturated or unsaturated fatty acids. These surfactants advantageously have at least one hydrophobic hydrocarbon chain having a number of carbons greater than 5 or even 10, and at least one hydrophilic anionic group, such as a sulphate, a sulphonate or a carboxylate linked to one end of the hydrophobic chain.

In the case where the surfactant is a cationic surfactant, it is chosen, for example, from alkylpyridium or alkylammonium halide salts such as n-ethyldodecylammonium chloride or bromide, cetylammonium chloride or bromide (CTAB). These surfactants advantageously have at least one hydrophobic hydrocarbon chain having a number of carbon atoms greater than 5 or even 10 and at least one hydrophilic cationic group, such as a quaternary ammonium cation.

In the case where the surfactant is a nonionic surfactant, it is for example chosen from polyoxyethylenated and/or polyoxypropylenated derivatives of fatty alcohols, fatty acids, or alkylphenols, arylphenols, or from alkylglucosides, polysorbates, cocamides.

According to one embodiment of the invention, the surfactant is sodium lauryl sulphate (SLS or SDS).

Preferably, the aqueous continuous phase of a dispersion according to the invention may comprise a mass content of surfactant(s) greater than 0.001%, and advantageously greater than 0.1%, by weight relative to the total weight of the dispersion.

Furthermore, the continuous aqueous phase of a dispersion according to the invention may comprise a mass content of surfactant(s) of less than 10.0%, and advantageously less than 1.0%, by weight relative to the total weight of the dispersion.

Shell of Drops

As mentioned above, the drops according to the invention are surrounded by a shell (or membrane) comprising at least one anionic polymer and at least one cationic polymer.

According to the invention, the drops obtained may have a very thin shell, in particular with a thickness less than 1% of the diameter of the drops.

The thickness of the shell is thus preferably less than 1 μm and is therefore too thin to be measured by optical methods.

According to one embodiment, the thickness of the shell of the drops is less than 1000 nm, in particular between 1 and 500 nm, preferably less than 100 nm, advantageously less than 50 nm, and more preferably less than 10 nm.

The measurement of the thickness of the shell of the drops of the invention may be carried out by the Small-Angle X-ray Scattering method, as implemented in Sato et al. J. Chem. Phys. 111, 1393-1401 (2007).

For this purpose, the drops are produced using deuterated water and are then washed three times with a deuterated oil, such as, for example, a deuterated hydrocarbon-type oil (octane, dodecane, hexadecane).

After washing, the drops are then transferred to the Neutrons cell to determine the I(q) spectrum; wherein q is the wave vector.

From this spectrum, conventional analytical treatments (REF) are applied to determine the thickness of the hydrogenated (undeuterated) shell.

According to one embodiment, the shell surrounding the drops of the dispersed phase is stiffened, which, in particular, gives good strength to the drops and reduces, or even prevents, their coalescence.

This shell is typically formed by coacervation, i.e. precipitation of polymers charged with opposite charges. Within a coacervate, the bonds binding the charged polymers to each other are of the ionic type, and are generally stronger than bonds present within a membrane of the surfactant type.

The shell is formed by coacervation of at least two charged polymers of opposite polarity (or polyelectrolyte) and preferably in the presence of a first polymer of the cationic type, and a second polymer, different from the first polymer, of the anionic type. These two polymers act as stiffening agents for the membrane.

The formation of the coacervate between these two polymers is generally the result of a modification of the conditions of the reaction medium (temperature, pH, reagent concentration, etc.). The coacervation reaction results from the neutralization of these two charged polymers of opposite polarities and allows the formation of a membrane structure by electrostatic interactions between the anionic polymer and the cationic polymer. The membrane thus formed around each drop typically forms a shell which completely encapsulates the core of the drop comprising the gelling agent(s), and thus isolates the core of the drop from the continuous aqueous phase.

Anionic Polymer

In the context of the present description, the term "anionic type polymer" or "anionic polymer" is understood to mean a polymer having anionic type chemical functions. We can also speak of anionic polyelectrolyte.

An "anionic chemical function" is understood to mean a chemical function AH capable of giving a proton to give a function A$^-$. Depending on the conditions of the medium in which it is found, the anionic type polymer therefore has chemical functions in AH form, or in the form of its conjugate base A$^-$.

As an example of anionic chemical functions, mention may be made of the carboxylic acid functions —COOH, optionally present in the form of carboxylate anion —COO$^-$.

As an example of an anionic type polymer, mention may be made of any polymer formed by the polymerization of monomers, at least a part of which carries anionic type chemical functions, such as carboxylic acid functions. Such monomers are, for example, acrylic acid, maleic acid, or any ethylenically unsaturated monomer containing at least one carboxylic acid function. It may for example be an anionic polymer comprising monomeric units comprising at least one chemical function of carboxylic acid type.

Preferably, the anionic polymer is hydrophilic, i.e. soluble or dispersible in water.

Examples of anionic polymer suitable for carrying out the invention include copolymers of acrylic acid or maleic acid and other monomers, such as acrylamide, alkyl acrylates and the like. $C_5$-$C_8$ alkyl acrylates, $C_{10}$-$C_{30}$ alkyl acrylates, $C_{12}$-$C_{22}$ alkyl methacrylates, methoxypolyethylene glycol methacrylates, hydroxyester acrylates, crosspolymer acrylates, and mixtures thereof.

According to the invention, an anionic polymer is preferably a carbomer as described below. This polymer may also be crosslinked copolymer acrylates/$C_{10-30}$ alkyl acrylate (INCI name: acrylates/$C_{10-30}$ alkyl acrylate crosspolymer).

According to one embodiment, the shell of the drops comprises at least one anionic polymer, such as for example a carbomer.

In the context of the invention, and unless otherwise stated, the term "carbomer" is understood to mean an optionally crosslinked homopolymer resulting from the polymerization of acrylic acid. It is therefore an optionally crosslinked poly(acrylic acid). Among carbomers of the invention, mention may be made of those sold under the names Tego® Carbomer 340FD from Evonik, Carbopol® 981 from Lubrizol, Carbopol ETD 2050 from Lubrizol or Carbopol Ultrez 10 from Lubrizol.

According to one embodiment, the term "carbomer" or "carbomer" or "Carbopol®" is understood to mean a high molecular weight acrylic acid polymer crosslinked with allyl sucrose or pentaerythritol allyl ethers (Handbook of Pharmaceutical Excipients, 5th Edition, p111). Examples include Carbopol®910, Carbopol®934, Carbopol®934P, Carbopol®940, Carbopol®941, Carbopol®71G, Carbopol®980, Carbopol®971P or Carbopol®974P. According to one embodiment, the viscosity of the carbomer is between 4,000 and 60,000 cP at 0.5% w/w.

The carbomers have other names: polyacrylic acids, carboxyvinyl polymers or carboxy polyethylenes.

A dispersion according to the invention may comprise from 0.01% to 5% by weight, preferably from 0.05% to 2%, and more preferably from 0.10% to 0.5%, of anionic polymer(s), in particular carbomer(s), relative to the total weight of the dispersion.

According to the invention, the dispersions according to the invention may comprise a carbomer and crosslinked acrylates/$C_{10-30}$ alkyl acrylate copolymer.

The aqueous phase according to the invention may also comprise at least one crosslinked polymer or at least one crosslinked copolymer, wherein the crosslinked polymer or crosslinked copolymer comprises at least one unit derived from the polymerization of one of the following monomers: acrylic or methacrylic acid, acrylate or alkyl methacrylate comprising from 1 to 30 carbon atoms, or their salts.

The aqueous phase may also comprise a mixture of crosslinked polymers or a mixture of crosslinked copolymers or a mixture of crosslinked polymer(s) and crosslinked copolymer(s).

According to the invention, the term "unit derived from the polymerization of a monomer" is understood to mean that the polymer or copolymer is a polymer or copolymer obtained by polymerization of the monomer.

According to one embodiment, the crosslinked polymer or the crosslinked copolymer is a crosslinked polyacrylate.

The crosslinked copolymers and polymers of the invention are anionic.

According to one embodiment, the copolymer is an unsaturated carboxylic acid copolymer and unsaturated $C_{1-30}$, preferably $C_1$-$C_4$, alkyl carboxylate. Such a copolymer comprises at least one hydrophilic unit of the olefinic unsaturated carboxylic acid type and at least one hydrophobic unit of the ($C_1$-$C_{30}$) alkyl ester type of unsaturated carboxylic acid.

Preferably, these copolymers are chosen from those whose hydrophilic unit of olefinic unsaturated carboxylic acid type corresponds to the following monomer of formula (I):

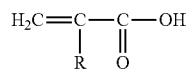

(I)

in which: $R_1$ denotes H or $CH_3$ or $C_2H_5$, i.e. units of acrylic acid, methacrylic acid or ethacrylic acid, and in which the hydrophobic unit of the ($C_1$-$C_{30}$) alkyl ester of unsaturated carboxylic acid type corresponds to the following monomer of formula (II):

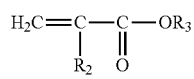

(II)

in which: $R_2$ denotes H or $CH_3$ or $C_2H_5$ (i.e. acrylate, methacrylate or ethacrylate units) and preferably H (acrylate units) or $CH_3$ (methacrylate units), $R_3$ denotes a $C_1$-$C_{30}$ alkyl radical; and preferably $C_1$-$C_4$.

Among this type of copolymer, those formed from a monomer mixture comprise:
(i) essentially acrylic acid,
(ii) an ester of formula (II) described above and in which $R_2$ denotes H or $CH_3$, wherein $R_3$ denotes an alkyl radical having from 1 to 4 carbon atoms,
(iii) and a crosslinking agent, which is a well-known copolymerizable polyethylenic unsaturated monomer, such as diallyl phthalate, trimethylolpropane tri(meth)acrylate, diallyl itaconate, diallyl fumarate, diallyl maleate, zinc (meth) acrylate, (meth) allyl acrylate, divinylbenzene, (poly) ethylene glycol dimethacrylate, methylene-bis-acrylamide, and castor oil.

According to one embodiment, the crosslinked polymer or the crosslinked copolymer is a polymer or copolymer of acrylic acid and/or methacrylic acid, and/or of alkyl acrylate comprising from 1 to 30 carbon atoms, preferably from 1 to 4 carbon atoms, and/or alkyl methacrylate comprising 1 to 30 carbon atoms, preferably 1 to 4 carbon atoms.

According to one embodiment, the crosslinked copolymer is a crosslinked copolymer of methacrylic acid and of alkyl acrylate comprising from 1 to 4 carbon atoms, preferably 2 carbon atoms.

In the context of the invention, and unless otherwise stated, the term "crosslinked copolymer of methacrylic acid and of alkyl acrylate comprising from 1 to 4 carbon atoms" is understood to mean a crosslinked copolymer resulting from the polymerization of a monomer of methacrylic acid and an alkyl acrylate monomer comprising from 1 to 4 carbon atoms.

Preferably, in this copolymer, the methacrylic acid is from 20% to 80% by weight, preferably from 35% to 65% by weight of the total weight of the copolymer.

Preferably, in this copolymer, the alkyl acrylate is from 15% to 80% by weight, preferably from 35% to 65% by weight of the total weight of the copolymer.

In particular, the alkyl acrylate is chosen from alkyl methacrylate, ethyl acrylate and butyl acrylate.

According to one embodiment, the crosslinked polymer or the crosslinked copolymer according to the invention and that is present in the continuous aqueous phase, is chosen from the group consisting of the following polymers or copolymers: Acrylates Copolymer, Acrylates crosspolymer-4, Acrylates crosspolymer-3, Polyacrylate-2 Crosspolymer and Polyacrylate-14 (INCI names).

Among the above polymers, according to the present invention, the products sold by LUBRIZOL under the trade names Fixate Superhold (INCI name=Polyacrylate-2 Crosspolymer), Fixate Freestyle Polymer (INCI name=Acrylates crosspolymer-3), Carbopol® Aqua SF1 (INCI name=Acrylates copolymer) and Carbopol® Aqua SF2 (INCI name=Acrylates crosspolymer-4).

Preferably, the crosslinked copolymer is Carbopol® Aqua SF1 (INCI name=Acrylates copolymer).

According to one embodiment, the crosslinked copolymer is chosen from crosslinked copolymers of acrylic or methacrylic acid and of alkyl acrylates comprising from 1 to 4 carbon atoms.

According to the invention, the dispersion of the invention may comprise from 0.1% to 10% by weight, preferably from 0.5% to 8% by weight, and preferably from 1% to 3% by weight of crosslinked polymer(s) or crosslinked copolymer(s) relative to the total weight of the dispersion.

According to the invention, the dispersions according to the invention may comprise a carbomer and a crosslinked copolymer Carbopol® Aqua SF1 (INCI name=Acrylates copolymer).

Cationic Polymer

According to one embodiment, the drops, and, in particular, the shell of the drops, further comprise a cationic type polymer. They may also comprise several cationic type polymers. This cationic polymer is the one mentioned above which forms the shell by coacervation with the anionic polymer.

In the context of the present application, and unless otherwise stated, the term "cationic polymer" or "cationic polymer" is understood to mean a polymer having chemical functions of cationic type. We may also speak of cationic polyelectrolyte.

Preferably, the cationic polymer is lipophilic or fat-soluble.

In the context of the present application, and unless otherwise stated, "chemical function of cationic type" is understood to mean a chemical function B capable of capturing a proton to give a function $BH^+$. Depending on the conditions of the medium in which it is located, the cationic type polymer therefore has chemical functions in form B, or in form $BH^+$, i.e. its conjugated acid.

As an example of chemical functions of the cationic type, mention may be made of the primary, secondary and tertiary amine functions, that are optionally present in the form of ammonium cations.

As an example of a cationic type polymer, may be mentioned any polymer formed by the polymerization of monomers, at least a part of which carries chemical functions of the cationic type, such as primary, secondary or tertiary amine functions.

Such monomers are, for example, aziridine, or any ethylenically unsaturated monomer containing at least one primary, secondary or tertiary amine function.

Examples of cationic polymers suitable for the implementation of the invention include amodimethicone, derived from a silicone polymer (polydimethylsiloxane, also called dimethicone), modified by primary amine and secondary amine functions.

Mention may also be made of amodimethicone derivatives, for example copolymers of amodimethicone, aminopropyl dimethicone, and more generally linear or branched silicone polymers containing amine functional groups.

The bis-isobutyl PEG-14/amodimethicone copolymer, bis (C13-15 Alkoxy) PG-Amodimethicone, Bis-Cetearyl Amodimethicone and bis-hydroxy/methoxy amodimethicone may be mentioned.

Mention may also be made of polysaccharide polymers comprising amine functions, such as chitosan or guar gum derivatives (hydroxypropyltrimonium guar chloride).

Mention may also be made of polypeptide polymers comprising amine functions, such as polylysine.

Mention may also be made of polyethyleneimine polymers comprising amine functions, such as linear or branched polyethyleneimine.

According to one embodiment, the drops, and, in particular, the shell of the drops, comprise a cationic polymer which is a silicone polymer modified with a primary, secondary or tertiary amine function, such as amodimethicone.

According to one embodiment, the drops, and, in particular, the shell of the drops, comprise amodimethicone.

According to a particularly preferred embodiment, the cationic polymer has the following formula:

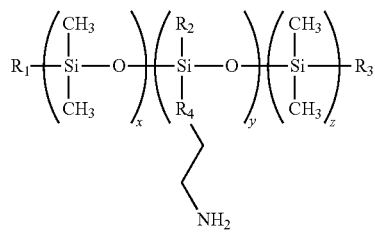

in which:
$R_2$ and $R_3$, independently of each other, represent OH or $CH_3$;
$R_4$ represents a group —$CH_2$— or a group —X—NH— in which X is a divalent alkylene radical $C_3$ or $C_4$;
x is an integer between 10 and 5000, preferably between 30 and 1000, and more preferably between 80 and 300;
y is an integer between 2 and 1000, preferably between 4 and 100, and more preferably between 5 and 20; and
z is an integer between 0 and 10, preferably between 0 and 1, and more preferably equal to 1.

In the aforementioned formula, when $R_4$ represents —X—NH—, X is attached to the silicon atom.

In the aforementioned formula, $R_1$, $R_2$ and $R_3$ are preferably $CH_3$.

In the aforementioned formula, $R_4$ is preferably a —$(CH_2)_3$—NH— group.

According to the invention, each drop may comprise from 0.01% to 10%, preferably from 0.05% to 5%, by weight of cationic polymer(s), in particular of amodimethicone(s), relative to the total weight of the fat phase.

Fatty Phase

According to the invention, the dispersions comprise a dispersed fatty phase, in the form of drops, comprising at least one gelling agent.

Gelling Agent

As indicated above, this invention is related to the presence in the dispersed fatty phase of at least one gelling agent. Such a gelling agent is different from the anionic and cationic polymers described above.

In the context of the invention, and unless otherwise indicated, the term "gelling agent" is understood to mean an agent for increasing the viscosity of the fatty phase of the drops of the dispersion free of the gelling agent, while, to reach a final viscosity, the gelled fatty phase greater than 20,000 mPa·s, preferably greater than 50,000 mPa·s, more preferably greater than 100,000 mPa·s, and more particularly greater than 200,000 mPa·s.

Preferably, the viscosity of the fatty phase of the drops of the dispersion in the presence of the gelling agent is between 20,000 and 100,000,000 mPa·s, preferably between 50,000 and 1,000,000 mPa·s, and more preferably between 100,000, at 500,000 mPa·s at 25° C.

The choice of gelling agent(s) takes place, in particular, with regard to the nature of the dispersed phase. Thus, for obvious reasons of compatibility, the gelling agent is lipophilic.

According to one embodiment, the gelling agent is chosen from lipophilic gelling agents as described below, wherein the solid fats at ambient temperature and pressure are chosen, in particular, from waxes, pasty fatty substances, butters, and their mixtures.

Lipophilic Gelling Agent(s)

The gelling agents that may be used according to the invention may be organic or inorganic, polymeric or molecular lipophilic gelling agents.

As inorganic lipophilic gelling agents, mention may be made of optionally modified clays, such as hectorites modified with a $C_{10}$ to $C_{22}$ ammonium chloride, such as hectorite modified with di-stearyl dimethyl ammonium chloride such as, for example, that sold under the name Bentone 38V® by the company ELEMENTIS. Mention may also be made of hectorite modified with distearyldimethylammonium chloride, also known as quaternium-18 bentonite, such as the products marketed or manufactured under the names Bentone 34 by the company Rheox, Claytone XL, Claytone 34 and Claytone 40 marketed or manufactured by Southern Clay, modified clays known as benzalkonium, and quaternium-18 bentonites and marketed or manufactured under the names Claytone HT, Claytone GR and Claytone PS by Southern Clay, chloride-modified clays of stearyldimethylbenzoylammonium, known as steralkonium bentonites, such as the products marketed or manufactured under the names Claytone APA and Claytone AF by Southern Clay, and Baragel 24 sold or manufactured by Rheox.

It is also possible to mention fumed silica optionally treated with a hydrophobic surface whose particle size is less than 1 μm. It is, in fact, possible to chemically modify the surface of the silica, by chemical reaction generating a decrease in the number of silanol groups present on the surface of the silica. In particular, it is possible to substitute silanol groups with hydrophobic groups, wherein a hydrophobic silica is then obtained.

The hydrophobic groups may be:
trimethylsiloxyl groups, which are obtained, in particular, by treating fumed silica in the presence of hexamethyldisilazane. Silicas thus treated are called "Silica silylate" according to the CTFA (8th edition, 2000). They are for example marketed under the references Aerosil R812® by the company DEGUSSA, CAB-O-SIL TS-530® by CABOT; or
dimethylsilyloxyl or polydimethylsiloxane groups, which are obtained, in particular, by treating fumed silica in the presence of polydimethylsiloxane or dimethyldichlorosilane. Silicas thus treated are called "Silica dimethyl silylate" according to the CTFA (8th edition, 2000). They are for example marketed under the references Aerosil R972® and Aerosil R974® by the company DEGUSSA, CAB-O-SIL TS-610® and CAB-O-SIL TS-720® by CABOT.

The hydrophobic fumed silica has, in particular, a particle size that may be nanometric to micrometric, for example ranging from about 5 to 200 nm.

Polymeric organic lipophilic gelling agents are, for example, partially or fully crosslinked elastomeric organopolysiloxanes of three-dimensional structure, such as those marketed under the names KSG6®, KSG16® and KSG18® by SHIN-ETSU, Dow Corning® EL-7040, Trefil E-505C® and Trefil E-506C® by DOW-CORNING, Gransil SR-CYC®, SR DMF10®, SR-DC556®, SR 5CYC Gel®, SR DMF 10 Gel® and SR DC 556 Gel® by the company GRANT INDUSTRIES, SF 1204® and JK 113® by the company General Electric; ethylcellulose such as that sold under the name Ethocel® by the company DOW CHEMICAL; galactomannans having from one to six, and in particular from two to four, hydroxyl groups per sac, substituted by a saturated or unsaturated alkyl chain, such as guar gum alkylated by $C_1$ to $C_6$ alkyl chains, and in particular $C_1$ to $C_3$ and mixtures thereof. Block copolymers of the "diblock", "triblock" or "radial" type of the polystyrene/polyisoprene, polystyrene/polybutadiene type, such as those sold under the name Luvitol HSB® by BASF, of the polystyrene/copoly (ethylene-propylene) type such as those sold under the name Kraton® by Shell Chemical Co. or else os the polystyrene/copoly (ethylene-butylene) type, mixtures of triblock and radial (star) copolymers in isododecane, such as those marketed by the PENRECO company under the name Versagel® such as the mixture of butylene/ethylene/styrene triblock copolymer and star copolymer ethylene/propylene/styrene in isododecane (Versagel M 5960).

According to one embodiment, the gelling agents that may be used according to the invention may be chosen from the group consisting of polyacrylates, esters of dextrin and fatty acid(s), esters of glycerol and of fatty acid(s), polyamides, and mixtures thereof.

Lipophilic gelling agents which may also be mentioned are polymers having a weight average molecular weight of less than 100,000, comprising a) a polymer backbone having hydrocarbon-based repeat units provided with at least one heteroatom, and optionally b) at least one fatty chain pendant and/or at least one optionally functionalized terminal fatty chain having from 6 to 120 carbon atoms and being bonded to these hydrocarbon units, as is described in applications WO 02/056847 and WO 02/47619, in particular the resins of polyamides (especially comprising alkyl groups having from 12 to 22 carbon atoms) such as those described in U.S. Pat. No. 5,783,657.

As an example of a polyamide resin that may be used according to the present invention, mention may be made of Uniclear 100 VG® marketed by ARIZONA CHEMICAL.

It is also possible to use polyorganosiloxane type silicone polyamides such as those described in U.S. Pat. Nos. 5,874,069, 5,919,441, 6,051,216 and 5,981,680.

These silicone polymers may belong to the following two families:
  polyorganosiloxanes comprising at least two groups capable of establishing hydrogen interactions, wherein these two groups are located in the polymer chain, and/or
  polyorganosiloxanes comprising at least two groups capable of establishing hydrogen interactions, wherein these two groups are located on grafts or branches.

Among the lipophilic gelling agents that may be used in the present invention, mention may also be made of dextrin and fatty acid esters, such as dextrin palmitates.

According to one embodiment, the ester of dextrin and fatty acid(s) according to the invention is a mono- or poly-ester of dextrin and of at least one fatty acid corresponding to the following formula (II):

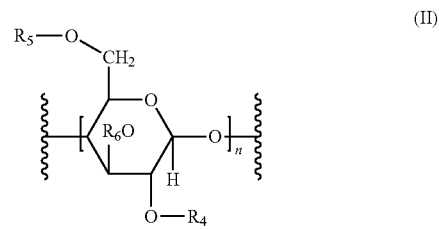

in which:
  n is an integer ranging from 2 to 200, preferably ranging from 20 to 150, and in particular ranging from 25 to 50,
  the radicals $R_4$, $R_5$ and $R_6$, which may be identical or different, are chosen from hydrogen or an acyl group —$COR_a$ in which the radical $R_a$ represents a hydrocarbon radical, linear or branched, saturated or unsaturated, having from 5 to 50, preferably from 5 to 25 carbon atoms,
  with the proviso that at least one of the $R_4$, $R_5$ and $R_6$ radicals is different from hydrogen.

According to one embodiment, $R_4$, $R_5$ and $R_6$ represent, independently of each other, H or an acyl group —$COR_a$ in which $R_a$ is a hydrocarbon radical as defined above, with the proviso that at least two of the radicals $R_4$, $R_5$ and $R_6$ are identical and different from hydrogen.

According to one embodiment, when the radicals $R_4$, $R_5$ and $R_6$, which are identical or different, represent a radical —$COR_a$, wherein these radicals may be chosen from the radicals caprylyl, caproyl, lauroyl, myristyl, palmityl, stearyl, eicosanyl, docosanoyl, isovaleryl, 2-ethylbutyryl, ethylmethylacetyl, isoheptanyl, 2-ethylhexanyl, isononanyl, isodemayyl, isotridemayyl, isomyristyl, isopalmityl, isostearyl, isohexanyl, decenyl, dodecenyl, tetradecenyl, myristyl, hexadecenoyl, palmitolyl, oleyl, elaidyl, eicosenyl, sorbyl, linoleyl, linolenyl, punicyl, arachidonyl, stearolyl, and mixtures thereof.

Among the esters of dextrin and fatty acid(s), mention may be made, for example, of dextrin palmitates, dextrin myristates, dextrin palmitates/ethylhexanoates and mixtures thereof.

Mention may, in particular, be made of the esters of dextrin and of fatty acid(s) marketed under the names Rheopearl® KL2 (INCI name: dextrin palmitate), Rheopearl® TT2 (INCI name: dextrin palmitate ethylhexanoate), and Rheopearl® MKL2 (INCI name: myristate dextrin) by Miyoshi Europe.

According to one embodiment, the gelling agent is chosen from polyacrylates resulting from the polymerization of $C_{10}$-$C_{30}$ alkyl acrylate(s), preferably of $C_{14}$-$C_{24}$ alkyl acrylate(s), and still more preferably $C_{18}$-$C_{22}$ alkyl acrylate(s).

According to one embodiment, the polyacrylates are polymers of acrylic acid esterified with a fatty alcohol whose saturated carbon chain comprises from 10 to 30 carbon atoms, preferably from 14 to 24 carbon atoms, or a mixture of the fatty alcohols. Preferably, the fatty alcohol comprises 18 carbon atoms or 22 carbon atoms.

Among the polyacrylates, may be mentioned more particularly stearyl polyacrylate, behenyl polyacrylate. Preferably, the gelling agent is stearyl polyacrylate or behenyl polyacrylate.

Mention may be made of polyacrylates sold under the names Interlimer® (INCI name: Poly $C_{10}$-$C_{30}$ alkyl acrylate), including Interlimer® 13.1 and Interlimer® 13.6 from the company Airproducts.

According to one embodiment, the gelling agent is an ester of glycerol and fatty acid(s), in particular a mono-, di- or triester of glycerol and fatty acid(s). Typically, the ester of glycerol and fatty acid(s) may be used alone or as a mixture.

According to the invention, it may be a glycerol ester and a fatty acid or a glycerol ester and a mixture of fatty acids.

According to one embodiment, the fatty acid is selected from the group consisting of behenic acid, isooctademayoic acid, stearic acid, eicosanoic acid, and mixtures thereof.

According to one embodiment, the ester of glycerol and fatty acid(s) has the following formula (I):

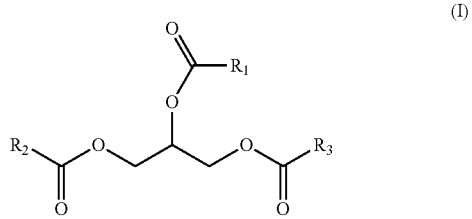

in which: $R_1$, $R_2$ and $R_3$ are, independently of one another, selected from H and a saturated alkyl chain comprising from 4 to 30 carbon atoms, wherein at least one of $R_1$, $R_2$ and $R_3$ is different from H.

According to one embodiment, $R_1$, $R_2$ and $R_3$ are different.

According to one embodiment, $R_1$, $R_2$ and/or $R_3$ represent(s) a saturated alkyl chain comprising from 4 to 30, preferably from 12 to 22, and more preferably from 18 to 22 carbon atoms.

According to one embodiment, the ester of glycerol and of fatty acid(s) corresponds to a compound of formula (I) in which $R_1$=H, $R_2$=$C_{21}H_{43}$ and $R_3$=$C_{19}H_{40}$.

According to one embodiment, the ester of glycerol and of fatty acid(s) corresponds to a compound of formula (I) in which $R_1$=$R_2$=$R_3$=$C_{21}H_{43}$.

According to one embodiment, the ester of glycerol and of fatty acid(s) corresponds to a compound of formula (I) in which $R_1$=$R_2$=H, and $R_3$=$C_{19}H_{40}$.

According to one embodiment, the ester of glycerol and of fatty acid(s) corresponds to a compound of formula (I) in which $R_1$=$R_2$=H, and $R_3$=$C_{17}H_{35}$.

Mention may in particular be made of the esters of glycerol and of fatty acid(s) marketed under the names Nomcort HK-G (INCI name: Glyceryl behenate/eicosadioate) and Nomcort SG (INCI name: Glyceryl tribehenate, isostearate, eicosadioate), by the Nisshin Oillio company.

Wax(es)

For the purposes of the invention, the term "wax" is understood to mean a lipophilic compound that is solid at room temperature (25° C.), with a reversible solid/liquid state change, having a melting point greater than or equal to 30° C. up to 120° C.

The protocol for measuring this melting point is described below.

The waxes that may be used in a composition according to the invention may be chosen from waxes that are solid, deformable or otherwise at room temperature, and are of animal, vegetable, mineral or synthetic origin, and mixtures thereof.

In particular, it is possible to use hydrocarbon-based waxes such as beeswax, lanolin wax, and Chinese insect waxes; rice wax, Carnauba wax, *Maydelilla* wax, Ouricurry wax, Alfa wax, cork fiber wax, sugar maye wax, Japanese wax and sumac wax; montan wax, microcrystalline waxes, paraffins and ozokerite; polyethylene waxes, waxes obtained by Fisher-Tropsch synthesis and waxy copolymers and their esters.

Mention may be made, in particular, of the waxes marketed under the names Kahlwax®2039 (INCI name: *Maydelilla cera*) and Kahlwax®6607 (INCI name: *Helianthus Annuus* Seed Wax) by the company Kahl Wachsraffinerie, Casid HSA (INCI name: Hydroxystearic Acid) by the CFPA SACI company, Performa®260 (INCI name: Synthetic wax) and Performa®103 (INCI name: Synthetic wax) by New Phase, and AJK-CE2046 (INCI name: Cetearyl alcohol, dibutyl lauroyl glutamide, dibutylethylhaxanoyl glutamide) by the company Kokyu Alcohol Kogyo.

Mention may also be made of waxes obtained by catalytic hydrogenation of animal or vegetable oils having linear or branched $C_8$-$C_{32}$ fatty chains.

Among these may be mentioned hydrogenated jojoba oil, hydrogenated sunflower oil, hydrogenated castor oil, hydrogenated coconut oil and hydrogenated lanolin oil, di-tetrastearate (trimethylol-1,1,1 propane) sold under the name "HEST 2T-4S" by the company HETERENE, di-(1,1,1-trimethylolpropane) tetraprenate sold under the name HEST 2T-4B by the company HETERENE.

It is also possible to use the waxes obtained by transesterifi-cation and hydrogenation of vegetable oils, such as castor oil or olive oil, such as the waxes sold under the names Phytowax ricin 16L64® and 22L73® and Phytowax Olive 18L57 from the company Sophim. Such waxes are described in application FR-A-2792190.

It is also possible to use silicone waxes, which may advantageously be substituted polysiloxanes, preferably at a low melting point.

Among the commercial silicone waxes of this type, mention may be made in particular of those sold under the names Abilwax 9800, 9801 or 9810 (GOLDSCHMIDT), KF910 and KF7002 (SHIN ETSU), or 176-1118-3 and 176-11481 (GENERAL ELECTRIC).

Silicone waxes that may be used may also be alkyl or alkoxydimethicones such as the following commercial products: Abilwax 2428, 2434 and 2440 (GOLDSCHMIDT), or VP 1622 and VP 1621 (WACKER), as well as ($C_{20}$-$C_{60}$) alkyldimethicones, in particular especially the ($C_{30}$-$C_{45}$) alkyldimethicones such as the silicone wax sold under the name SF-1642 by the company GE-Bayer Silicones.

It is also possible to use hydrocarbon waxes modified with silicone or fluorinated groups such as, for example, siliconyl maydelilla, siliconyl beeswax and Fluorobeeswax by Koster Keunen.

The waxes may also be chosen from fluorinated waxes.

Butter(s) or Pasty Fatty Substance

For the purposes of the present invention, the term "butter" (also referred to as "pasty fatty substance") is understood to mean a lipophilic fatty compound with a reversible solid/liquid state change and comprising a liquid fraction and a solid fraction at a temperature of 25° C. and atmospheric pressure (760 mmHg). In other words, the starting melting temperature of the pasty compound may be less than 25° C. The liquid fraction of the pasty compound measured at 25° C. may represent from 9% to 97% by weight of the compound. This liquid fraction at 25° C. is preferably between 15% and 85%, more preferably between 40 and 85% by weight. Preferably, the one or more butters have an end-of-melting temperature of less than 60° C. Preferably, the butter(s) has/have a hardness less than or equal to 6 MPa.

Preferably, the butters or pasty fatty substances have an anisotropic crystalline organization in the solid state that is visible by X-ray observations.

For the purposes of the invention, the melting temperature corresponds to the temperature of the endothermic peak observed in thermal analysis (DSC) as described in ISO 11357-3; 1999. The melting point of a paste or a wax may be measured using a differential scanning calorimeter (DSC), for example the calorimeter sold under the name "DSC Q2000" by the company TA Instruments.

With respect to the measurement of the melting temperature and the determination of the end-of-melting temperature, the sample preparation and measurement protocols are as follows: A sample of 5 mg of pasty fatty substance (or butter) or wax previously heated to 80° C. and taken with magnetic stirring using an equally-heated spatula is placed in an airtight aluminum capsule or crucible. Two tests are carried out to ensure the reproducibility of the results.

The measurements are made on the calorimeter mentioned above. The oven is subjected to a nitrogen sweep. The cooling is ensured by the RCS 90 heat exchanger. The sample is then subjected to the following protocol, first being brought to a temperature of 20° C. and then subjected to a first temperature rise ranging from 20° C. to 80° C. at the heating rate of 5° C./minute, then cooled from 80° C. to −80° C. at a cooling rate of 5° C./minute, and finally subjected to a second temperature rise from −80° C. to 80° C. at a heating rate of 5° C./minute. During the second temperature rise, the variation of the power difference absorbed by the empty crucible and the crucible containing the butter sample is measured as a function of the temperature. The melting point of the compound is the value of the temperature corresponding to the peak of the curve representing the variation of the difference in power absorbed as a function of the temperature. The end-of-melting temperature corresponds to the temperature at which 95% of the sample melted.

The liquid fraction by weight of the butter (or pasty fatty substance) at 25° C. is equal to the ratio of the enthalpy of fusion absorbed at 25° C. over the enthalpy of melting of the butter. The enthalpy of melting of the butter or pasty compound is the enthalpy absorbed by the compound to pass from the solid state to the liquid state.

The butter is said to be in the solid state when the entirety of its mass is in crystalline solid form. The butter is said to be in the liquid state when the entirety of its mass is in liquid form. The melting enthalpy of the butter is equal to the integral of the whole of the melting curve obtained with the aid of the proposed calorimeter, with a rise in temperature of 5° C. or 10° C. per minute, according to the standard ISO 11357-3: 1999. The melting enthalpy of the butter is the amount of energy required to pass the compound from the solid state to the liquid state. It is expressed in J/g.

The enthalpy of melting absorbed at 25° C. is the amount of energy absorbed by the sample to change from the solid state to the state it exhibits at 25° C. consisting of a liquid fraction and a solid fraction. The liquid fraction of the butter measured at 32° C. preferably represents from 30% to 100% by weight of the compound, preferably from 50% to 100%, more preferably from 60% to 100% by weight of the compound. When the liquid fraction of the butter measured at 32° C. is 100%, the temperature of the end of the melting range of the pasty compound is less than or equal to 32° C. The liquid fraction of the butter measured at 32° C. is equal to the ratio of the enthalpy of melting absorbed at 32° C. to the enthalpy of melting of the butter. The enthalpy of melting absorbed at 32° C. is calculated in the same way as the enthalpy of melting absorbed at 23° C.

As regards the measurement of the hardness, the sample preparation and measurement protocols are as follows: the composition according to the invention or the butter is placed in a mold that is 75 mm in diameter and is filled to about 75% of its height. In order to overcome the thermal past and control the crystallization, the mold is placed in the Vötsch VC0018 programmable oven where it is first heated to 80° C. for 60 minutes, then cooled from 80° C. to 0° C. at a cooling rate of 5° C./minute, then left at the stabilized temperature of 0° C. for 60 minutes, then subjected to a temperature rise from 0° C. to 20° C., at a rate of heat of 5° C./minute, then left at the stabilized temperature of 20° C. for 180 minutes. The compression force measurement is performed with Swantech's TA/TX2i texturometer. The spindle used is chosen according to the texture: —cylindrical steel spindle 2 mm in diameter for very rigid raw materials; —cylindrical steel spindle 12 mm in diameter for rigid raw materials. The measurement comprises 3 steps: a first step after automatic detection of the surface of the sample where the spindle moves at the measuring speed of 0.1 mm/s, and enters the composition according to the invention or the butter to a penetration depth of 0.3 mm, wherein the software records the value of the maximum force reached; a second so-called relaxation stage wherein the spindle stays at this position for one second and wherein the force is noted after 1 second of relaxation; finally a third so-called withdrawal step where the spindle returns to its initial position at a speed of 1 mm/s and the energy of withdrawal of the probe (negative force) is noted.

The value of the hardness measured in the first step corresponds to the maximum compression force measured in Newton divided by the surface area of the texturometer cylinder expressed in $mm^2$ in contact with the butter or the composition according to the invention. The value of hardness obtained is expressed in mega-pascals or MPa.

The pasty fatty substance or butter may be chosen from synthetic compounds and compounds of plant origin. A pasty fatty substance may be obtained synthetically from starting materials of plant origin.

The pasty fatty substance is advantageously chosen from:
  lanolin and its derivatives such as lanolin alcohol, oxyethylenated lanolines, acetylated lanolin, lanolin esters such as isopropyl lanolate, oxypropylenated lanolines,
  polymeric or non-polymeric silicone compounds, such as polydimethylsiloxanes of high molecular weight, polydimethylsiloxanes with side chains of the alkyl or alkoxy type having from 8 to 24 carbon atoms, especially stearyl dimethicones,
  polymeric or non-polymeric fluorinated compounds,
  vinyl polymers, in particular
  homopolymers of olefins,
  olefin copolymers,
  homopolymers and copolymers of hydrogenated dienes,
  linear or branched oligomers, homo or copolymers of alkyl (meth) acrylates preferably having a $C_8$-$C_{30}$ alkyl group,
  homo and copolymeric oligomers of vinyl esters having $C_8$-$C_{30}$ alkyl groups, homo and copolymer oligomers of vinyl ethers having $C_8$-$C_{30}$ alkyl groups, the liposoluble polyethers resulting from the polyetherification between one or more $C_2$-$C_{100}$ and preferably $C_2$-$C_{50}$ diols, esters and polyesters, and their mixtures.

According to a preferred embodiment of the invention, the particular butter(s) is/are of plant origin such as that/those described in Ullmann's Encyclopedia of Industrial Chemistry ("Fats and Fatty Oils", A. Thomas, published on 15 Jun. 2000, D01: 10.1002/14356007.a10_173 point 13.2.2.2. Shea Butter, Borneo Tallow, and Related Fats (Vegetable Butters).

More particularly may be mentioned triglycerides $C_{10}$-$C_{18}$ (INCI name: $C_{10}$-$C_{18}$ Triglycerides) comprising a liquid fraction and a solid fraction at a temperature of 25° C. and at atmospheric pressure (760 mm Hg), shea butter, Nilotica Shea butter (*Butyrospermum parkii*), Galam butter, (*Butyrospermum parkii*), Borneo butter or fat or Tengkawang tallow) (*Shorea stenoptera*), *Shorea* butter, Illipé butter, *Madhuca* butter or *Bassia Madhuca longifolia*, mowrah butter (*Madhuca Latifolia*), Katiau butter (*Madhuca motleyana*), Phulwara butter (*M. butyracea*), mango butter (*Mangifera indica*), Murumuru butter (*Astrocatyum murumuru*), Kokum butter (*Garcinia Indica*), Ucuuba butter (*Virola sebifera*), Tucuma butter, Painya butter (Kpangnan) (*Pentadesma butyracea*), coffee butter (*Coffea arabica*), Apricot butter (*Prunus Armeniaca*), Macadamia butter (*Macadamia Temifolia*), butter butter grape (*Vitis vinifera*), avocado butter (*Persea gratissima*), olive butter (*Olea europaea*), sweet almond butter (*Prunus amygdalus dulcis*), cocoa butter (*Theobroma cacao*) and sunflower butter, butter under the INCI name *Astrocaryum Murumuru* Seed Butter, butter under the INCI name *Theobroma Grandiflorum* Seed Butter, and butter under the INCI name *Irvingia Gabonensis* Kernel Butter, jojoba esters (mixture of wax and oil hydrogenated jojoba) (INCI name: Jojoba esters), and ethyl esters of shea butter (INCI name: Shea butter ethyl esters), and mixtures thereof.

Preferably, the gelling agent is chosen from dextrin palmitates.

Advantageously, a fat-phase gelling agent according to the invention is a heat-sensitive gelling agent, i.e. one that reacts with heat, and, in particular, is a gelling agent that is solid at room temperature and liquid at a temperature above 40° C., preferably above 50° C.

Advantageously, a fatty phase gelling agent according to the invention is a thixotropic gelling agent or one that is capable of conferring a thixotropic behavior on the solution which comprises it.

Such a thixotropic gelling agent is, in particular, chosen from the pyrogenic silicas, optionally hydrophobically treated, described above.

According to one embodiment, a dispersion according to the invention may comprise from 0.1% to 75%, preferably from 0.5% to 60%, in particular from 1% to 40%, more preferably from 1.5% to 20%, and most preferably from 1% to 4%, by weight of gelling agent(s) relative to the total weight of the dispersion.

According to the invention, a dispersion according to the invention may comprise from 0.5% to 99.99%, preferably from 1% to 70%, in particular from 1.5% to 50%, more preferably from 2% to 40% by weight, particularly preferably from 2.5% to 30%, and most preferably from 10% to 20%, by weight of gelling agent(s) relative to the total weight of the fatty phase.

Oil(s)

According to the invention, the fatty phase of a dispersion according to the invention may further comprise at least one oil H1, preferably in which the cationic polymer is soluble. The oil H1, therefore, advantageously corresponds to a good solvent of the cationic polymer.

The dispersions according to the invention may comprise a single oil H1 or a mixture of several oils H1. A dispersion according to the invention may, therefore, comprise at least one, at least two, at least three, at least four, at least five or more oil(s) H1 as described below.

The term "oil" is understood to mean a fatty substance that is liquid at ambient temperature (25° C.).

As oils H1 used in the composition of the invention, mention may be made, for example:

hydrocarbon oils of animal origin, such as perhydrosqualene and squalane;

esters and synthetic ethers, in particular of fatty acids, such as the oils of formulas $R_1COOR_2$ and $R_1OR_2$ in which $R_1$ represents the residue of a $C_8$ to $C_{29}$ fatty acid, and $R_2$ represents a hydrocarbon chain, branched or unbranched, $C_3$ to $C_{30}$, such as, for example, purcellin oil, isononyl isononanoate, isodecyl neopentanoate, isopropyl myristate, 2-ethylhexyl palmitate, octyl-2 stearate dodecyl, octyl-2-dodecyl erucate, isostearyl isostearate; hydroxylated esters such as isostearyl lactate, octyl hydroxystearate, octyldodecyl hydroxystearate, diisostearyl malate, triisocetyl citrate, heptanoates, octanoates, demayoates of fatty alcohols; polyol esters, such as propylene glycol dioctanoate, neopentyl glycol diheptanoate and diethylene glycol diisononanoate; and pentaerythritol esters such as pentaerythrityl tetrahehenate (DUB PTB) or pentaerythrityl tetraisostearate (Prisorine 3631);

linear or branched hydrocarbons of mineral or synthetic origin, such as paraffin oils, volatile or not, and their derivatives, petroleum jelly, polydecenes, hydrogenated polyisobutene such as Parleam oil;

silicone oils, for example volatile or non-volatile polymethylsiloxanes (PDMS) with a linear or cyclic silicone chain, which are liquid or pasty at room temperature, in particular cyclopolydimethylsiloxanes (cyclomethicones) such as cyclohexasiloxane and cyclopentasiloxane; polydimethylsiloxanes (or dimethicones) comprising alkyl, alkoxy or phenyl groups, during or at the end of the silicone chain, groups having from 2 to 24 carbon atoms; phenyl silicones such as phenyltrimethicones, phenyldimethicones, phenyltrimethylsiloxy-diphenylsiloxanes, diphenyldimethi-cones, diphenylmethyldiphenyltrisiloxanes, 2-phenylethyltrimethylsiloxysilicates, and polymethylphenylsiloxanes;

fatty alcohols having from 8 to 26 carbon atoms, such as cetyl alcohol, stearyl alcohol and their mixture (cetylstearyl alcohol), or else octyldodemayol;

partially fluorinated hydrocarbon oils and/or silicone oils such as those described in document JP-A-2-295912; and their mixtures.

According to one embodiment, the oil H1 is chosen from the esters of formula $R_1COOR_2$, in which $R_1$ represents the residue of a $C_8$ to $C_{29}$ fatty acid, and $R_2$ represents a hydrocarbon chain, branched or unbranched, at $C_3$ to $C_{30}$.

According to one embodiment, the oil H1 is chosen from fatty alcohols having from 8 to 26 carbon atoms.

According to one embodiment, the oil H1 is chosen from hydrocarbon oils having from 8 to 16 carbon atoms, and in particular $C_8$-$C_{16}$ branched alkanes (also known as isoparaffins or isoalkanes), such as isododemaye (also called 2,4,4,6-pentamethylheptane), isodemaye, isohexademaye, and, for example, the oils sold under the trade names Isopars® or Permethyls®.

According to a preferred embodiment, the oil H1 is chosen from the group consisting of isononyl isononanoate, dimethicone, isohexademaye, polydimethylsiloxane, octyldodemayol, isodecyl neopentanoate and their mixtures.

Preferably, the oil H1 is isononyl isononanoate.

According to one embodiment, the oil H1 is not a vegetable oil.

According to one embodiment, the oil H1 is not represented by polydimethylsiloxane (PDMS), and is preferably not a silicone oil.

According to another embodiment, the fatty phase of the drops does not comprise polydimethylsiloxane (PDMS), and preferably does not include silicone oil.

According to a preferred embodiment, a dispersion according to the invention may comprise at least 1% by weight of oil(s) H1, preferably isononyl isononanoate, relative to the total weight of the composition.

According to one embodiment, the content of oil(s) H1 in the fatty phase is between 1% and 99.49%, preferably between 20% and 90%, and in particular between 30% and 60%, by weight relative to the total weight of the fatty phase.

According to one embodiment, the fatty phase of the dispersions according to the invention may further comprise at least one hydrocarbon oil H2 of plant origin. The fatty phase may comprise several oils H2.

As vegetable oils H2, particular mention may be made of liquid triglycerides of $C_4$-$C_{10}$ fatty acids such as triglycerides of heptanoic or octanoic acids, or else, for example, sunflower, corn, soybean, squash, coconut and grape, sesame, hazelnut, apricot, macadamia, arara, castor, avocado, caprylic/capric acid triglycerides (INCI name: Caprylic/Capric Triglyceride) such as those marketed by Stearineries Dubois or those available under the trade names "Miglyol 810", "Miglyol 812" and "Miglyol 818" by Dynamit Nobel, jojoba oil, or shea butter oil.

Among the oils H2, mention may also be made of the following compounds: $C_{10}$-$C_{18}$ triglycerides which are liquid at room temperature (25° C.), triglycerides of caprylic and capric acids, triglycerides of caprylic acid, capric acid, myristic acid and stearic (INCI name: Caprylic/capric/ myristic/stearic Triglyceride), triethylhexanoine, hydrogenated vegetable oil, meadowfoam seed oil *Limnanthes Alba* (INCI name: *Limnanthes Alba* (Meadowfoam) Seed Oil), olive oil *Olea Europaea* (INCI name: *Olea Europaea* (Olive) Fruit Oil), *Macadamia* nut oil (INCI name: *Macadamia Ternifolia* Seed Oil), Rosa Mayina rosehip oil (INCI name: Rosa Mayina Fruit Oil), soybean oil (INCI name: *Glycine Soja* (Soybean) Oil), sunflower seed oil (INCI name: *Helianthus Annuus* (Sunflower) Seed Oil), corn oil (INCI name: *Zea Mays* (Corn) Oil), hydrogenated palm oil (INCI name: Hydrogenated Palm Oil), tribneinine (INCI name: tribehenin), triisostearin (INCI name: triisostearin), apricot kernel oil (INCI name: *Prunus Armeniaca* (Apricot) Kernel Oil), rice bran oil (INCI name: *Oryza Sativa* (Rice) Bran Oil), argan oil (INCI name: *Argania Spinosa* Kernel Oil), avocado oil (INCI name: *Persea Gratissima* Oil), evening primrose oil (INCI name: *Oenothera Biennis* Oil), palm oil (INCI name: *Elaeis Guineensis* Oil), rice germ oil (INCI name: *Oryza Sativa* Germ Oil), hydrogenated coconut oil (INCI name: Hydrogenated Coconut Oil), sweet almond oil (INCI name: *Prunus Amygdalus Dulcis* Oil), grape seed oil (INCI name: *Vitis Vinifera* Seed Oil), sesame seed oil (INCI name: *Sesamum Indicum* Seed Oil), peanut seed oil (INCI name: *Arachis Hypogaea* Oil), hydrogenated rapeseed oil (INCI name: Hydrogenated Rapeseed Oil), *Mortierella isabellina* oil (INCI name: *Mortierella* Oil), Safflower Seed Oil (INCI name: *Carthamus Tinctorius* Seed Oil), Queensland *Macadamia integrifolia* nut oil (INCI name: *Macadamia Integrifolia* Seed Oil), tricaprylin (or triacylglycerol), vegetable oil (INCI name: Olus Oil), palm oil extracted from the nucleus (INCI name: *Elaeis Guineensis* Kernel Oil), coconut oil (INCI name: *Cocos Nucifera* Oil), wheat (INCI name: *Triticum Vulgare* Germ Oil), borage seed oil (INCI name: *Borago Officinalis* Seed Oil), shea oil (INCI name: *Butyrospermum Parkii* Oil), hazelnut oil (INCI name: *Corylus Avellana* Seed Oil), hydrogenated castor oil (INCI name: Hydrogenated Castor Oil), hydrogenated palm kernel oil (INCI name: Hydrogenated Palm Kernel Oil), mango seed oil (INCI name: *Mangifera Indica* Seed Oil), Pomegranate Seed Oil (INCI name: *Punica Granatum* Seed Oil), Seed Oil Chinese cabbage (INCI name: *Brassica Campestris* Seed Oil), passion fruit seed oil (INCI name: *Passiflora Edulis* Seed Oil), *camellia* seed oil from Japan (INCI name: *Camellia Japonica* Seed Oil), green tea seed oil (INCI name: *Camellia Sinensis* Seed Oil), corn germ oil (INCI name: *Zea Mays* Germ Oil), oil of hoplostete (INCI name: *Hoplostethus* Oil), Brazil nut oil (INCI name: *Bertholletia Excelsa* Seed Oil), musk rose seed oil (INCI name: *Rosa Moschata* Seed Oil), Inca Inchi seed oil (or *Sacha Inchi*) (INCI name: *Plukenetia Volubilis* Seed Oil), Babassu seed oil (INCI name: *Orbignya Oleifera* Seed Oil), the seed oil of a hybrid sunflower strain (INCI name: *Helianthus Annuus* Hybrid Oil), the Sea buckthorn oil (INCI name: *Hippophae Rhamnoides* Oil), Marula seed oil (INCI name: *Sclerocarya Birrea* Seed Oil), *Aleurites Molu* seed oil cmaya (INCI name: *Aleurites Molucmaya* Seed Oil), Ruby Seed Oil (INCI Name: *Rosa Rubiginosa* Seed Oil), *Camellia Kissi* Seed Oil (INCI Name: *Camellia Kissi* Seed Oil), Oil of baobab seed (INCI name: *Adansonia Digitata* Seed Oil), baobab oil (INCI name: *Adansonia Digitata* Oil), Moringa seed oil (INCI name: *Moringa Pterygosperma* Seed Oil), shell oil perilla (INCI name: *Perilla Ocymoides* Seed Oil), castor seed oil (INCI name: *Ricinus Communis* Seed Oil), mayola oil (INCI name: Mayola Oil), black currant seed oil (INCI name: *Ribes Nigrum* Seed Oil), tea seed oil (INCI name: *Camellia Oleifera* Seed Oil), raspberry seed oil (INCI name: *Rubus ldaeus* Seed Oil), crambe seed oil of Abyssinia (INCI name: *Crambe Abyssinica* Seed Oil), rosehip seed oil (INCI name: Rosa Mayina Seed Oil), viper plant leaved oil n (INCI name: *Echium Plantagineum* Seed Oil), tomato seed oil (INCI name: *Solanum Lycopersicum* Seed Oil), bitter almond oil (INCI name: *Prunus Amygdalus Amara* Kernel Oil), oil of yuzu seed (INCI name: *Citrus Junos* Seed Oil), pumpkin seed oil (INCI name: *Cucurbita Pepo* Seed Oil), *Mustela* Mustelidae mink oil (INCI name: *Mustela* Oil), desert date palm seed (INCI name: *Balanites Roxburghii* Seed Oil), *Brassica Napus* seed oil (INCI name: *Brassica Napus* Seed Oil), Calophyllum oil (INCI name: *Calophyllum Inophyllum* Seed Oil), arctic black seed oil (INCI name: *Rubus Chamaemorus* Seed Oil), Japanese white pine seed oil (INCI name: *Pinus Pentaphylla* Seed Oil), watermelon seed oil (INCI name: *Citrullus Lanatus* Seed Oil), walnut seed oil (INCI name: *Juglans Regia* Seed Oil), *nigella* seed oil (INCI name: *Nigella Sativa* Seed Oil), carrot seed oil (INCI name: *Daucus Carota Sativa* Seed Oil), *Coix Lacryma*-jobi Ma-yuen seed oil (INCI name: *Coix Lacryma-*Jobi Ma-yen Seed Oil), I *Coix Lacryma*-jobi seed oil (INCI name: *Coix Lachryma*-Jobi Seed Oil), the lipid mixture of *Triticum Vulgare* flour (INCI name: *Triticum Vulgare* Flour Lipids), trihydroxymethoxystearin (INCI name: Trihydroxymethoxystearin), triheptanoine (INCI name: *Triheptanoin*), cranberry seed oil (INCI name: *Vaccinium Macrocarpon* Seed Oil), vanilla oil (INCI name: *Vanilla Planifolia* Fruit Oil), cranberry seed oil (INCI name: *Oxycoccus Palustris* Seed Oil), Acai oil (INCI name: *Euterpe Oleracea* Fruit Oil), triester of hydrogenated castor oil and isostearic acid (INCI name: Hydrogenated Castor Oil Triisostearate), hydrogenated cottonseed oil (INCI name: Hydrogenated Cottonseed Oil), hydrogenated olive oil (name IN CI: Hydrogenated Olive Oil), hydrogenated peanut oil (INCI name: Hydrogenated Peanut Oil), hydrogenated soybean oil (INCI name: Hydrogenated Soybean Oil), oil extracted from chicken egg yolk (INCI name: Egg Yolk Oil), peach kernel core oil (INCI name: *Prunus Persica* Kernel Oil), glycerides from mayola oil and phytosterols (INCI name: *Phytosteryl Mayola* Glycerides), black currant seed (INCI name: *Ribes Nigrum* (Black Currant) Seed Oil), karanja seed oil (INCI name: *Pongamia Glabra* Seed Oil) and roucou oil (INCI name: Roucou (*Bixa orellana*) Oil), olive oil extract, especially phytosqualane, rosehip oil, coriander oil, flaxseed oil, chia oil, fenugreek oil, hemp, and their mixtures.

Preferably, the oil H2 is chosen from those rich in polyunsaturated fatty acids.

For the purposes of the present invention, the term "unsaturated fatty acid" is understood to mean a fatty acid comprising at least one double bond. It more particularly relates to long chain fatty acids, i.e. that may have more than 14 carbon atoms. The unsaturated fatty acids may be in acid form, or in salt form, for example their calcium salt, or in the form of derivatives, in particular of fatty acid ester(s).

Preferably, the oil H2 is chosen from oils that are rich in long-chain fatty acids, i.e. able to have more than 14 carbon atoms, and, better, unsaturated fatty acids containing from 18 to 22 carbon atoms, especially ω-3 and ω-6 fatty acids. Thus, advantageously, the vegetable oils are chosen from evening primrose, borage, blackcurrant seed, hemp, walnut, soybean, sunflower, wheat germ, fenugreek, rosebush and muscat echium, argan, baobab, rice bran, sesame, almond, hazelnut, chia, flax, olive, avocado, safflower, coriander, rapeseed (in particular *Brassica naptus*), and their mixtures.

Preferably, the oil H2 is chosen from matt and non-glossy oils. In particular, mention may be made of Moringa oil.

According to one embodiment, the content of oil(s) H2 in the fatty phase of a dispersion according to the invention is between 0% and 40%, preferably between 0.1% and 25%, and in particular between 1% and 20%, by weight relative to the total weight of the fatty phase.

According to one embodiment, the mass ratio between the amount of oil(s) H1 and the amount of oil(s) H2 is from 0.025 to 99.49, preferably from 0.8 to 90, and in particular from 2.5 to 80.

The fatty phase may further comprise at least one other oil different from the oils H1 and H2.

A dispersion according to the invention may comprise from 0.0001% to 50%, preferably from 0.1% to 40%, and better still from 1% to 25%, by weight of oil(s) relative to the total weight of the dispersion.

Additional Compound(s)

According to the invention, the aqueous continuous phase and/or the dispersed fatty phase may furthermore comprise at least one additional compound other than the anionic and cationic polymers, the gelling agent and the aforementioned oils.

The dispersions according to the invention, and in particular the continuous aqueous phase and/or the dispersed fatty phase of the dispersions, may furthermore comprise powders, flakes, dyes, particulate agents insoluble in the fatty phase, elastomers of silicone emulsifiers and/or non-emulsifiers, especially as described in EP 2,353,577, preservatives, humectants, stabilizers, chelators, emollients, modifying agents chosen from texturizing agents, viscosity agents (for example, gelling agents/aqueous phase texture different from the abovementioned base), pH, osmotic force and/or refractive index modifiers etc. . . . or any usual cosmetic additive, and mixtures thereof.

According to one embodiment, the particulate agents that are insoluble in the fatty phase of the drops are chosen from the group consisting of pigments, ceramics, polymers, especially acrylic polymers, and mixtures thereof.

The dispersions according to the invention, and, in particular, the continuous aqueous phase and/or the dispersed fatty phase of the dispersions, may furthermore comprise at least one biological/cosmetic active agent chosen from moisturizing agents, healing agents and depigmenting agents, UV filters, desquamating agents, antioxidants, active agents stimulating the synthesis of dermal and/or epidermal macromoleculars, dermodecontracting agents, antiperspirants, soothing agents and/or anti-aging agents, and mixtures thereof.

Anti-Wrinkle or Anti-Aging Agents

As representative of anti-wrinkle or anti-aging agents that may be used in the present invention, mention may be made more particularly of adenosine, retinol and its derivatives, ascorbic acid and its derivatives, such as magnesium ascorbyl phosphate and ascorbyl glucoside; tocopherol and its derivatives, such as tocopheryl acetate; nicotinic acid and its precursors, such as nicotinamide; ubiquinone; glutathione and its precursors, such as L-2-oxothiazolidine-4-carboxylic acid; C-glycoside compounds and their derivatives, as described in particular below; plant extracts and, in particular, extracts of sea fennel and olive leaf, as well as vegetable proteins and their hydrolysates, such as hydrolysates of rice or soya proteins; or *Vigna aconitifolia* seed extracts such as those marketed by Cognis under the references Vitoptine LS9529 and Vit-A-Like LS9737; algae extracts and, in particular, laminaria; bacterial extracts; sapogenins, such as diosgenin and extracts of Dioscorea, in particular Wild Yam, containing it; α-hydroxy acids; β-hydroxyacids, such as salicylic acid and n-octanoyl-5-salicylic acid; oligopeptides and pseudodipeptides and their acyl derivatives, in particular {2-[acetyl-(3-trifluoromethyl-phenyl)-amino]-3-methyl-butyrylamino}-acetic acid and the lipopeptides marketed by SEDERMA under the trade names Biopeptide CL, Matrixyl 500 and Matrixyl 3000; lycopene; manganese and magnesium salts, in particular gluconates; rye seed extract under the trade name Coheliss de Silab, an extract of *Centella asiatica* leaves; oily or aqueous extracts of *vanilla planifolia* fruit, *vanilla planifolia* flower extract; and their mixtures.

Humectants or Moisturizers

Among humectants or moisturizers, mention may be made of glycerin; diglycerin; glycols, such as sorbitol; betaines; urea and its derivatives including Hydrovance® marketed by National Starch; monosaccharides such as mannose, AHA, BHA, beta-glumay and in particular sodium carboxymethyl beta-glumay from Mibelle-AG-Biochemistry; polyoxybutylene, polyoxyethylene, or polyoxypropylene glycerol such as WILBRI DE S-753L® from NOF corporation; muscat rose oil marketed by Nestle; spheres of collagen and chondroitin sulfate of marine origin (Ateocollagen) marketed by Engelhard Lyon under the name marine filling spheres; niacinamide; Sederma glyceryl polymethacrylate sold under the trade name Lubragel®; trimethylglycine sold under the trade name Aminocoat® by the company Ashahi Kasei Chemicals; mother-of-pearl extracts containing a conchyoline sold in particular by the company Maruzen (Japan) under the trade name Pearl Extract®; plant extracts such as an extract of *Castanea sativa* or aqueous or oily extracts of *Camellia japonica* flower and in particular of the variety alba plena; hydrolysed hazelnut proteins; polysaccharides of *Polyanthes tuberosa; Argania spinosa* core oil; homo- and co-polymers of 2-methacryloyloxyethylphosphorylcholine acid, such as Lipidure HM and Lipidure PBM from NOF; saccharides such as glucose, fructose, mannose or trehalose; glycosaminoglymays and their derivatives such as hyaluronic acid, sodium hyaluronate and acetylated hyaluronic acid, in particular spheres of hyaluronic acid such as those marketed by Engelhard Lyon; panthenol; allantoin; the aloe vera; free amino acids and their derivatives; glucosamine; citric acid; ceramides; and their mixtures.

Antioxidants

Among antioxidants, mention may be made more particularly of tocopherol and its esters, in particular tocopherol acetate; EDTA, ascorbic acid and its derivatives, in particular ascorbyl magnesium phosphate, ascorbyl glucoside and 3-O-ethyl ascorbic acid; chelating agents, such as BHT, BHA, N, N' bis (3,4,5-trimethoxybenzyl) ethylenediamine and its salts, and mixtures thereof.

Depigmenting Agents

As depigmenting agents, mention may be made of ceramides, vitamin C and its derivatives, and especially the vit CG, CP and 3-O ethyl vitamin C, alpha and beta arbutin, ferulic acid, kojic acid, resorcinol and its derivatives and in particular 4-butyl resorcinol, tranexamic acid and its derivatives, D calcium panthein sulfonate, lipoic acid, ellagic acid, vitamin B3, phenylethyl resorcinol such as Symwhite 377® from the company Symrise, a kiwi fruit water (*Actinidia chinensis*) marketed by Gattefosse, an extract of *Paeonia suffructicosa* root such as that marketed by the company Ichimaru Pharcos under the name Botanpi Liquid B®, a licorice extract (*Glycyrrhiza glabra*) extract, an extract of brown sugar (*Saccharum officinarum*), such as the molasses extract marketed by the company Taiyo Kagaku under the name Molasses Liquid, a mixture of undecylenic acid and phenylalanine undecylenoyl, such as Sepiwhite's Sepiwhite MSH®.

Of course, those skilled in the art will take care to choose any additional compound(s) and/or their quantity in such a way that the advantageous properties of the dispersion according to the invention are not, or not substantially, altered by the addition envisaged. In particular, the nature and/or the amount of the additional compound(s) depends on the aqueous or fatty nature of the phase in question of the dispersion according to the invention. These adjustments are within the competence of a person skilled in the art.

According to one embodiment, the dispersion according to the invention comprises from 0.00020% to 10%, preferably from 0.00025% to 5%, and more preferably from 0.0026% to 1% by weight, and especially of dye(s), based on the total weight of the dispersion.

Among preservatives, may be mentioned phenoxyethanol, pentylene glycol and EDTA.

According to one embodiment, the dispersions according to the invention comprise at least one preservating agent, and preferably a mixture of several preserving agents.

Preferably, the content by weight of preservatig agent(s) is from 0.01% to 10%, preferably from 0.5% to 5%, relative to the total weight of the dispersion.

According to the invention, a dispersion according to the invention, and, in particular, the core of the drops (i.e. the fatty phase), may also comprise at least one perfuming agent.

Among the perfuming agents, mention may be made of any type of perfume or fragrance, these terms being used here indifferently. These perfumes or fragrances are well known to those skilled in the art and include, in particular, those mentioned, for example, in S. Arctander, Perfume and Flavor Chemicals (Montclair, N.J., 1969), S. Arctander, Perfume and Flavor Materials of Natural Origin. (Elizabeth, N.J., 1960) and in "Flavor and Fragrance Materials," 1991 (Allured Publishing Co. Wheaton, Ill. USA). The perfumes used in the context of the present invention may include natural products such as extracts, essential oils, absolutes, resinoids, resins, concretes, etc. as well as basic synthetic substances such as hydrocarbons, alcohols aldehydes, ketones, ethers, acids, esters, acetals, ketals, nitriles, etc., including saturated and unsaturated compounds, aliphatic, alicyclic and heterocyclic compounds.

The dispersion according to the invention may comprise from 0.01% to 30% by weight of perfuming agent(s), preferably from 0.5% to 20% by weight, relative to the total weight of the dispersion.

According to one embodiment, the dispersions of the invention may further comprise glycerine. Preferably, a dispersion according to the invention may comprise at least 5% by weight of glycerol relative to the total weight of the dispersion.

In fact, beyond the texture, the dispersions according to the invention offer another advantage over "conventional" emulsions because they allow the use of glycerin, moreover in high levels.

They may, in particular, comprise glycerin in a content greater than or equal to 10%, greater than or equal to 20%, greater than or equal to 30%, greater than or equal to 40%, or even up to 50% by weight, relative to the total weight of the dispersion.

Preparation Method

The dispersions according to the invention may be prepared by various methods.

Thus, the dispersions according to the invention have the advantage of being able to be prepared according to a simple "non-microfluidic" method, i.e. by simple emulsification.

As in the case of a conventional emulsion, an aqueous solution and a fatty solution are prepared separately. It is the stirring addition of the fatty phase in the aqueous phase which creates the direct emulsion.

The viscosity of the aqueous phase may be controlled, in particular by varying the amount of anionic polymer (especially carbomer) and the pH of the solution. In general, the pH of the aqueous phase is less than 4.5, which may involve the final addition of a third sodium hydroxide solution (BF) to reach a pH of between 5.5 and 6, 5.

The viscosity of the aqueous phase and the shear force applied to the mixture are the two main parameters that influence the size and monodispersity of the emulsion.

The emulsions according to the invention may also be prepared according to a microfluidic method, in particular as described in the international applications WO 2012/120043 or WO 2015/055748.

According to this embodiment, the drops obtained by this microfluidic method have a uniform size distribution.

Preferably, the dispersions of the invention consist of a population of monodisperse drops, in particular wherein they have an average diameter $\overline{D}$ of from 1 μm to 2500 μm, or even from 500 µm to 3000 µm, and a coefficient of variation Cv less than 10%, or even less than 3%.

In the context of the present description, the term "monodisperse drops" is understood to mean that the population of drops of the dispersion according to the invention has a uniform size distribution. Monodisperse drops offer good monodispersity. Conversely, drops with poor monodispersity are said to be "polydispersed".

According to one approach, the average diameter of the drops is, for example, measured by analysis of a photograph of a batch consisting of N drops using image processing software (Image J). Typically, according to this method, the diameter is measured in pixels, then converted to µm, depending on the size of the container containing the drops of the dispersion.

Preferably, the value of N is chosen to be greater than or equal to 30, so that this analysis reflects in a statistically significant manner the drop diameter distribution of the emulsion.

The diameter $D_i$ of each drop is measured and the average diameter $\overline{D}$ obtained by calculating the arithmetic mean of these values:

$$\overline{D} = \frac{1}{N}\sum_{i=1}^{N} D_i$$

From these $D_i$ values, one may also obtain the standard deviation σ of the diameters of the drops of the dispersion:

$$\sigma = \sqrt{\frac{\sum_{i=1}^{N}(D_i - \overline{D})^2}{N}}$$

The standard deviation σ of a dispersion reflects the distribution of the diameters $D_i$ of the drops of the dispersion around the average diameter $\overline{D}$.

Knowing the mean diameter $\overline{D}$ and the standard deviation a of a dispersion, one may determine that 95.4% of the drop population is found in the diameter range [$\overline{D}-2\sigma;\overline{D}+2\sigma$] and that 68.2% of the population is found in the range [$\overline{D}-\sigma; \overline{D}+\sigma$].

To characterize the monodispersity of the dispersion according to this approach of the invention, the coefficient of variation may be calculated:

$$C_v = \frac{\sigma}{\overline{D}}$$

This parameter reflects the distribution of the diameters of the drops as a function of the average diameter thereof.

The coefficient of variation Cv of the diameters of the drops according to this mode of the invention is less than 10%, preferably less than 5%, or even less than 3%.

Alternatively, the monodispersity may be demonstrated by placing a dispersion sample in a bottle of constant circular section. A gentle stirring by rotating a quarter of a turn for half a second around the axis of symmetry passing through the bottle, followed by a rest of half a second is performed, before repeating the operation in the opposite direction, wherein this is repeated four times in a row.

The drops of the dispersed phase are organized in a crystalline form when they are monodispersed. Thus, they have a stack in a repeating pattern in three dimensions. It is then possible to observe a regular stack which indicates good monodispersity, or an irregular stack reflecting the polydispersity of the dispersion.

To obtain monodisperse drops, it is also possible to use the microfluidic technique (Utada et al., MRS Bulletin 32, 702-708 (2007), Cramer et al., Chem Sci 59, 15, 3045-3058). (2004)), and more particularly microfluidic devices of the co-flow type (the fluids go in the same direction) or flow-focusing devices (the fluids go in different directions, and typically in opposite directions).

The presence, in the fatty phase, of gelling agent(s), as envisaged above, may require adjustments in the method for preparing a dispersion according to the invention. In particular, the method for preparing such a dispersion according to the invention may comprise a heating step (between 40° C. and 150° C., in particular between 50° C. and 90° C.) of the fatty phase before mixing/contacting the fatty phase with the aqueous phase and, if appropriate in the case of a "non-microfluidic" method as mentioned above, maintaining this heating during stirring until the desired emulsion is obtained. In the case of a "microfluidic" method as mentioned above, this heating step takes place at least during the fatty phase and the microfluidic device during the manufacture of the dispersion.

According to one embodiment, the method for preparing the dispersions of the invention comprises a drop-forming step comprising:
  contacting an aqueous fluid FE and an oily fluid FI as defined above; and
  the formation of drops of fatty phase, consisting of the oily fluid FI, dispersed in a continuous aqueous phase, consisting of fluid FE, wherein the drops comprise a shell insulating the core of the drops of the fatty phase of the dispersion.

According to one embodiment, the fluid FI is initially prepared by mixing a fatty phase intended to form the core of the drops, at least a first precursor polymer of the coacervation such as a cationic polymer as defined above, at least one gelling agent and further, optionally, at least one oil and/or at least one additional compound as mentioned above.

According to one embodiment, the fluid FE is initially prepared by mixing an aqueous phase intended to form the continuous phase of the dispersion, at least one second polymer precursor of the coacervation, such as an anionic polymer as defined previously and furthermore, optionally, at least one base, an additional compound, preservatives and/or other water-soluble products such as, for example, glycerin.

According to one embodiment, the cationic polymer initially present in the oily fluid FI serves, in particular, for the formation of the shell of the drops.

According to one embodiment, the aqueous continuous phase of the dispersion formed comprises, or is represented by, the aqueous phase of the fluid FE. The anionic polymer initially present in the fluid FE is used, in particular, for the formation of the shell of the drops. The anionic polymer also contributes to increasing the viscosity of the fluid FE, and therefore of the continuous aqueous phase.

According to one embodiment, the drop formation step may further comprise a step of injecting a solution for increasing the viscosity of the continuous aqueous phase of the fluid FE. Preferably, the viscosity increasing solution is aqueous. This solution for increasing the viscosity is typically injected into the aqueous external fluid FE after formation of the dispersion according to the invention, and thus after formation of the drops.

According to one embodiment, the solution for increasing the viscosity comprises a base, in particular an alkaline hydroxide, such as sodium hydroxide.

According to one embodiment, the method for preparing a dispersion according to the invention comprises a step of heating the oily fluid F1 comprising the fatty phase of the dispersion, at a temperature of between 40° C. and 150° C., preferably between 50° C. to 90° C., prior to the aforementioned step of forming the drops, and therefore before mixing/contacting the fatty phase with the aqueous phase. In the case of a "non-microfluidic" method as mentioned above, this heating step may be maintained during stirring to obtain the desired emulsion. In the case of a "microfluidic" method as mentioned above, this heating step takes place at least at the level of the fatty phase and the microfluidic device during the manufacture of the dispersion.

According to one embodiment, the temperature of the heating step is from 50° C. to 90° C., or even from 50° C. to 80° C., preferably from 50° C. to 70° C., and more preferably from 55° C. to 70° C., or even 55° C. to 65° C.

According to one embodiment, when the oily fluid FI comprises from 5% to 15% by weight of gelling agent(s), in particular heat-sensitive, relative to the total weight of the oily fluid FI, the oily fluid FI is heated to a temperature of 65 to 70° C.

According to one embodiment, when the oily fluid FI comprises from 15% to 99.99%, preferably from 15% to 40%, by weight of gelling agent(s) relative to the total weight of the oily fluid FI, the oily fluid FI is heated to a temperature of 80 to 90° C.

According to this embodiment, the method for preparing the dispersions of the invention comprises the following steps:
- optionally heating the oily fluid FI as described above to a temperature of from 40° C. to 150° C., preferably from 50° C. to 90° C.;
- contacting the aqueous fluid FE as described above with the oily fluid FI; and
- the formation of fatty phase drops, consisting of the oily fluid FI, dispersed in a continuous aqueous phase consisting of fluid FE, wherein the drops comprise a shell insulating the core of the drops of the fatty phase of the dispersion.

Advantageously, the presence of a gelling agent in the oily fluid FI makes it possible to dispense with the use of an intermediate fluid as described in the application WO 2012/120043. This emerges, in particular, from Example 1 below. In this, the method for preparing a dispersion according to the invention is simplified with respect to the preparation method described in WO 2012/120043.

Uses

In a preferred manner, a dispersion according to the invention is directly usable, at the end of the aforementioned preparation methods, as a composition, in particular a cosmetic composition. The dispersion according to the invention may also be used as a composition, in particular a cosmetic composition. Thus, according to one particular embodiment, the dispersion according to the invention, when prepared by means of a microfluidic method as described above, may be used as a composition after separation of the drops and redispersion thereof in a second appropriate phase.

The dispersions or compositions according to the invention may, in particular, be used in the cosmetics field.

The invention thus also relates to the use of a dispersion according to the invention for the preparation of a composition, in particular a cosmetic composition.

The dispersions or compositions according to the invention may comprise, in addition to the aforementioned ingredients, at least one physiologically acceptable medium.

The present invention thus also relates to a composition, in particular a cosmetic composition, comprising at least one dispersion according to the invention, in combination with a physiologically acceptable medium.

In the context of the invention, and unless otherwise stated, the term "physiologically acceptable medium" is understood to mean a medium that is suitable for cosmetic applications, and that is particularly suitable for applying a composition of the invention to a keratin material, in particular the skin and/or the hair, and more particularly the skin.

The physiologically acceptable medium is generally adapted to the nature of the support to which the composition is to be applied, as well as to the appearance under which the composition is to be packaged.

According to one embodiment, the physiologically acceptable medium is directly represented by the aqueous continuous phase as described above.

The cosmetic compositions of the invention may be, for example, a cream, an emulsion, a lotion, a serum, a gel and an oil for the skin (hands, face, feet, etc.), a foundation (liquid, paste), a preparation for baths and showers (salts, foams, oils, gels, etc.), a hair care product (hair dye and bleach), a cleaning product (lotions, powders, shampoos), a cleaning product for the hair (lotions, creams, oils), a styling product (lotions, lacquers, brilliantines), a product for shaving (soaps, foams, lotions, etc.), a product intended to be applied to the lips, a solar product, a sunless tanning product, a product that whitens the skin, an anti-wrinkle product. In particular, the cosmetic compositions of the invention may be an anti-aging serum, a youth serum, a moisturizing serum or a scented water.

The present invention also relates to a non-therapeutic method for the cosmetic treatment of a keratin material, in particular the skin and/or the hair, and more particularly the skin, comprising a step of applying to the keratin material at least one dispersion or at least one layer of a cosmetic composition mentioned above.

The dispersions of the invention, in particular the shell of the drops of the dispersions, advantageously have improved mechanical strength with respect to these same dispersions but free of the gelling agent in the dispersed fatty phase (as, for example, the dispersions described in the document WO 2012/120043).

This improved mechanical strength makes it possible to avoid shearing or fragmentation of the drops during the transport of dispersions or cosmetic products containing them.

In addition, this improvement in the mechanical strength advantageously makes it possible to condition the dispersions and the cosmetic products by comprising them in packaging that may comprise air without the risk of shearing and/or fragmentation.

In addition, the dispersions according to the invention advantageously have stability properties similar to identical dispersions free from gelling agent(s) in the fatty phase, such as for example the dispersions described in the document WO 2012/120043.

The dispersions of dispersed drops according to the invention advantageously have viscosities compatible with easy handling of the product obtained.

Throughout the description, including the claims, the phrase "comprising one" should be understood as being synonymous with "comprising at least one", unless the opposite is specified.

The expressions "between . . . and . . . ", "from . . . to . . . " and "from . . . to . . . " are to be understood as being inclusive, unless specified otherwise.

The amounts of the ingredients in the examples are expressed as percentage by weight relative to the total weight of the composition, unless otherwise indicated.

The examples which follow illustrate the present invention without limiting its scope.

EXAMPLES

Equipment

| Equipment | Use |
| --- | --- |
| 2 syringe pumps | Microfluidic device |
| Peristaltic pumps | |
| 50 mL glass syringes | |
| 25 mL glass syringe | |
| Syringe heater | |
| 3 3-way valves | |
| PTFE capillary | |
| 1 device | Microfluidic device |
| 1 central tower | Supply support |
| 1 stand | Microfluidic device support |
| Stirring motor | Preparation of the solutions |
| Thermostatic magnetic heating plate | |
| Scales | |
| Lab consumables | Regular use |

Unless otherwise indicated, the compositions described hereinafter result from a microfluidic method, in particular as described in the description or in WO/2010/063937.

Example 1

Preparation of a Dispersion of Drops with or without the Use of Intermediate Fluid This example consisted in preparing a dispersion by a method carried out in the presence of an intermediate phase called MF (Comparative Example 1A) or in its absence (Example 1B according to the invention).

The compositions of the phases (fluids) allowing the preparation of the dispersions 1A and 1B are as follows:

| Fluid | Name | INCI | 1A (comparison) % w/w | 1B (invention) % w/w |
| --- | --- | --- | --- | --- |
| IF | Lanol 99 | Isononyl Isononanoate | SQF* | SQF* |
| | Rheopearl KL2 | Dextrin Palmitate | 0.5/5/10 | 0.5/5/10 |
| | KF 8004 | Amodimethicone | 0.5 | 0.5 |
| MF | Lanol 99 | Isononyl Isononanoate | 100 | — |
| OF ($\mu$ = 811 pH = 3.48) | Osmosis water | — | 83.34 | 83.34 |
| | Glycerol | Glycerin | 7.00 | 7.00 |
| | Zemea | Propanediol | 6.00 | 6.00 |
| | Microcare PTG | Pentyleneglycol | 2.35 | 2.35 |
| | Microcare PE | Phenoxyethanol | 0.95 | 0.95 |
| | Carbomer Tego 340 FD | Carbomer | 0.24 | 0.24 |
| | Rhodicare T | Xanthan | 0.12 | 0.12 |
| Base | Osmosis water | Aqua | 99.7 | 99.7 |
| | NaOH | Sodium Hydroxyde | 0.3 | 0.3 |

*SQF: sufficient quantity for

Preparation Protocol

For the OF:
The carbomer is dispersed in osmosis water and stirred for 2 hours with a pale deflocculant.
Glycerin, Propanediol (Zemea) as well as xanthan are subsequently added. Following these additions, the mixture is stirred for 10 min.
Phenoxyethanol (Microcare PE) and Pentylene Glycol (Microcare PTG) are added. The mixture is stirred for 5 minutes.
Soda is then added.
The last step is to mix the solution for 1 hour.
For the base: The soda and water are mixed using a magnetic bar for 5 min.
For the IF:
Amodimethicone is added to Lanol 99 then mixed with a magnetic bar for 5 min.
The mixture is heated to 80° C. and Rheopearl KL2 is then added with magnetic stirring.
This mixture may then be placed in a water bath heated to 75° C. with magnetic stirring for 1 hour.
The IF solution heated to 75° C. is introduced into a syringe connected to a heater to keep the solution hot. To reduce heat loss, the microfluidic device was installed directly at the syringe outlet. The amount of gelling agent was modified: 0.5%, 5% and 10% by weight relative to the total weight of the IF phase.
To stabilize the system, mounting was used one hour after introduction of the IF solution into the syringe.

Example 1A

In this test 1A (carried out in the presence of an intermediate phase MF), the following flow rates were used:

| OF | 240 mL/hr |
| --- | --- |
| MF | 5 mL/hr |
| IF | 15 mL/hr |
| Base | 28.8 mL/hr |

The presence of the Rheopearl KL2 gelling agent led to an opacification of the drops of the dispersion. In addition, regardless of the gelling agent concentration, the appearance of the drops obtained did not prove to be uniform. It has been demonstrated that according to this method, the gelling agent has not diffused through the MF and has not gelled the fatty phase in its entirety.

Example 1B

Another test 1B was carried out with IF containing 10% Rheopearl KL2 and without MF intermediate phase, with the following flow rates:

| OF | 240 mL/hr |
| --- | --- |
| MF | 0 mL/hr |
| IF | 20 mL/hr |
| Base | 28.8 mL/hr |

By implementing a method free of intermediate phase, it has been shown that the drops of the final dispersion have a completely uniform appearance.

The stability over time of the MF-free (i.e. according to the invention) assay system 1B was investigated. For this, a production of the dispersion of drops was carried out under the same conditions as the test 1A and the diameter of the drops was measured over time. An identical diameter throughout the manipulation ensures that no parameters were changed. In fact, a fouling of the nozzle or a viscosity change of the IF would have been automatically detected by a change in the size of the bubbles. The results obtained are as follows:

TABLE 1

Measurement of diameters during dispersion production including gelled drops

| Time (min) | 5 | 30 | 60 | 120 | 180 | 240 | 300 |
|---|---|---|---|---|---|---|---|
| Mean diameter* (mm) | 1.221 | 1.200 | 1.192 | 1.211 | 1.213 | 1.222 | 1.249 |
| Covariance (%) | 4.471 | 2.895 | 2.885 | 2.471 | 2.046 | 2.586 | 2.852 |

*Measurements made on 100 drops

The covariance of the mean diameters over time is 1.07%. The difference in diameter is negligible.

The microfluidic method used without MF intermediate phase is stable. It may be assumed that the presence of the oily gelling agent slows the diffusion of the amodimethicone at the water/oil interface and prevents fouling of the nozzle. The use of an intermediate phase is therefore not necessary in contrast to obtaining a microfluidic dispersion with the comparative composition 1A.

Example 2

Mechanical Strength of Drop Dispersions Comprising a Gelling Agent 2.1. Transport Test With regard to the mechanical strength of the dispersions according to the invention, a transport test was carried out on a serum sample with 20% of Rheopearl KL2 in the oily phase. For this purpose, a conventional 100 ml receptacle that does not require a specific atmosphere free of air is filled to 50% with the sample.

| Trade name | INCI name | Percentage in phase (% m) | Final mass percentage (% m) |
|---|---|---|---|
| Aqueous phase | | | |
| Osmosis water | Aqua | 86.09% | 78.80% |
| Glycérine | Glycerin | 5.80% | 5.31% |
| Zemea | Butylene glycol | 5.00% | 4.58% |
| Microcare PTG | Pentylenglycol | 2.00% | 1.83% |
| Rhodicare T | Xanthan gum | 0.10% | 0.09% |
| Microcare PE | Phenoxyethanol | 0.79% | 0.72% |
| Carbomer Tego 340 FD | Carbomer | 0.20% | 0.18% |
| Sodium hydroxyde pellets PRS codex | Sodium hydroxyde | 0.03% | 0.03% |
| Total | | 100.00% | 91.54% |
| Fat phase | | | |
| Lanol 99 | Isononyl isononanoate | 79.10% | 6.69% |
| Rheopearl KL2 | Dextrin palmitate | 20.00% | 1.69% |
| KF 8004 | Amodimethicone | 0.50% | 0.04% |
| Phat Blue DC 6204 | CI 61565/CI 60725 | 0.40% | 0.03% |
| Total | | 100.00% | 8.458% |
| TOTAL | | | 100.00% |

This transport test consists of a round trip Marseille-Paris, by the Post Office.

It was observed that the drops of the dispersion, subjected to this transport test, were not fragmented: they therefore remained intact despite the use of non-airless packaging.

2.2. Rolling Test

A rolling test was performed on the following two different samples:
1st sample=dispersion 2A: gelled drops with 10% Rheopearl KL2 in IF (according to the invention)
2nd sample=dispersion 2B: ungelled drops (without Rheopearl KL2) in the IF (comparative)

Composition of the 1st Sample:

| Trade name | INCI name | % m in the phase | % m final |
|---|---|---|---|
| Aqueous phase | | | |
| Osmosis water | Aqua | SQF * | SQF * |
| Glycerine | Glycerine | 16.152 | 14.844 |
| Zemea | Propanediol | 5.384 | 4.948 |
| Butylène glycol | Butylene glycol | 5.384 | 4.948 |
| Microcare PTG | Pentylenglycol | 2.146 | 1.972 |
| Microcare PE | Phenoxyethanol | 0.858 | 0.789 |
| Carbomer Tego 340FD | Carbomer | 0.233 | 0.214 |
| EDETA | Disodium EDTA | 0.037 | 0.034 |
| Sodium hydroxyde pellets PRS codex | Sodium hydroxyde | 0.043 | 0.039 |
| Total | | 100 | 91.900 |
| FATTY PHASE | | | |
| DUB ININ | Isononyl isononanoate | SQF * | SQF * |
| Rheopearl KL2 | Dextrin palmitate | 10 | 0.810 |
| KF 8004 | Amodimethicone | 0.5 | 0.041 |
| Phat Blue DC 6204 | CI 61565, CI 60725 | 0.01 | <0.01 |
| Total | | 100 | 8.100 |
| Total | | | 100.00 |

* SQF: sufficient quantity for

Composition of the 2nd Sample:

| Trade name | INCI name | % m in the phase | % m final |
|---|---|---|---|
| Aqueous phase | | | |
| Osmosis water | Aqua | SQF * | SQF * |
| Glycerine | Glycerine | 16.152 | 14.844 |
| Zemea | Propanediol | 5.384 | 4.948 |
| Butylène glycol | Butylene glycol | 5.384 | 4.948 |
| Microcare PTG | Pentylenglycol | 2.146 | 1.972 |
| Microcare PE | Phenoxyethanol | 0.858 | 0.789 |
| Carbomer Tego 340FD | Carbomer | 0.233 | 0.214 |
| EDETA | Disodium EDTA | 0.037 | 0.034 |
| Sodium hydroxyde pellets PRS codex | Sodium hydroxyde | 0.043 | 0.039 |
| Total | | 100 | 91.900 |
| FAT PHASE | | | |
| DUB ININ | Isononyl isononanoate | SQF * | SQF * |
| KF 8004 | Amodimethicone | 0.5 | 0.041 |
| Phat Blue DC 6204 | CI 61565, CI 60725 | 0.01 | <0.01 |
| Total | | 100 | 8.100 |
| Total | | | 100.00 |

* SQF: sufficient quantity for

Operating Procedure of the Rolling Test

A line is traced at 4 cm high on a glass pot 8.5 cm high and 4 cm in diameter. For both samples, the drops were collected up to this limit line. Each pot was then placed at room temperature for 1 week.

After this time, each jar was gently tilted horizontally and allowed to stand for one hour. They were then placed on the rollers of a roller-mixer. The different rotation cycles were imposed according to the order below:

6 rpm for 3 min
20 rpm for 3 min
30 rpm for 3 min
30 rpm for 1 hour

Visual observation of both samples was performed during the shear to describe the elasticity of the membrane. Another observation was also made between each cycle to study bubble fragmentation.

Observations

| Protocol | Dispersion 2B Protocol not comprising gelling agent (comparative) | Dispersion 2A comprising a gelling agent (invention) |
|---|---|---|
| 6 rpm for 3 min | No fragmentation | No fragmentation |
| 20 rpm for 3 min | No fragmentation | No fragmentation |
| 30 rpm for 3 min | Slight fragmentation + deformation of the drops. Some drops have a behavior: irreversible deformation reversible deformation | No fragmentation |
| 30 rpm for 1 h | Strong fragmentation over time For 25 min, the drops deform and fragment After 25 min: the drops immediately fragment into multiple fine droplets After 40 minutes: It is difficult to distinguish the drops. The drops are almost destroyed. | No fragmentation The drops remain intact for 1 hour |

It was thus shown that the dispersion 2A according to the invention has a better mechanical strength than the same dispersion 2B devoid of gelling agent.

2.3. Ball Test

Protocol

A stainless steel ball was placed in a vial of 12 ml containing a composition and the behavior of the drops at the passage of the ball was studied.

Two vials were thus prepared, respectively comprising the dispersions 2A and 2B described in the rolling test 2.2 above.

Observations

The passage of the ball on the composition 2B (comparative) not comprising a gelling agent led to some fragmentation of the ungelled drops. The composition 2A (according to the invention) containing drops comprising a gelling agent was found to be very resistant to the passage of the ball. No deformation or fragmentation was observed for composition 2A. After several passes of the ball, the ungelled sample 2B showed a strong fragmentation that was not observed for the sample 2A with the gelled drops.

Example 3

Preparation of a Care Serum

The composition 3A (according to the invention) is a composition whose drops of fatty phase comprise a gelling agent. It was prepared from the following phase compositions (see table below):

Composition 3A

| Fluid | Name | INCI | % w/w |
|---|---|---|---|
| OF ($\mu$ = 552 mPa·s pH = 4.60) | Osmosis water | — | 67.63 |
| | Glycerol | Glycerine | 17.31 |
| | Zemea | Propanediol | 5.77 |
| | Butylène Glycol | Butylene glycol | 5.77 |
| | Microcare PTG | Pentyleneglycol | 2.3 |
| | Microcare PE | Phenoxyethanol | 0.92 |
| | Carbomer Tego 340 FD | Carbomer | 0.25 |
| | EDETA | Disodium EDTA | 0.04 |
| | NaOH | Hydroxyde de sodium | 0.01 |
| Base | Osmosis water | Water | 99.5 |
| | NaOH | Sodium hydroxyde | 0.5 |
| IF (gelled) | Lanol 99 | Isononyl Isononanoate | 89.35 |
| | Rheopearl KL2 | Dextrin Palmitate | 10 |
| | KF 8004 | Amodimethicone | 0.5 |
| | Phat Black DC 9206 | CI 61565, CI 60725, CI 26100 | 0.15 |

The composition 3B (comparative) is a composition whose fatty phase drops do not comprise a gelling agent. It was prepared from the following phase compositions (see table below):

Composition 3B

| Fluid | Name | INCI | % w/w |
|---|---|---|---|
| OF ($\mu$ = 552 mPa·s pH = 4.60) | Osmosis water | — | 67.63 |
| | Glycerol | Glycerine | 17.31 |
| | Zemea | Propanediol | 5.77 |
| | Butylene Glycol | Butylene glycol | 5.77 |
| | Microcare PTG | Pentyleneglycol | 2.3 |
| | Microcare PE | Phenoxyethanol | 0.92 |
| | Carbomer Tego 340 FD | Carbomer | 0.25 |
| | EDETA | Disodium EDTA | 0.04 |
| | NaOH | Sodium hydroxyde | 0.01 |
| Base | Osmosis water | Water | 99.5 |
| | NaOH | Sodium hydroxyde | 0.5 |
| IF (non gelled) | Lanol 99 | Isononyl Isononanoate | 99.35 |
| | KF 8004 | Amodimethicone | 0.5 |
| | Phat Black DC 9206 | CI 61565, CI 60725, CI 26100 | 0.15 |
| MF | Lanol 99 | Isononyl Isononanoate | 100 |

Protocol of Preparation

For the OF:

The carbomer is dispersed in the osmosis water and agitated for 2 hours using a pale deflocculator, Glycerine, Zemea as well as butylene glycol are subsequently added. Following these additions, the mixture is stirred for 10 minutes, Microcare PE, Microcare PTG and EDETA are added. The mixture is stirred for 5 minutes.

Soda is then added.

The last step is to mix the solution for 1 hour.

For the Base: The soda and water are mixed using a magnetic bar for 5 min.

For the Gelled IF:

Amodimethicone is added to Lanol 99 then mixed with a magnetic bar for 5 min.

The mixture is heated to 80° C. and Rheopearl KL2 is then added with magnetic stirring.

Phat Black DC 9206 dye is then added to the composition. This mixture may then be placed in a water bath heated to 75° C. with magnetic stirring for 1 hour.

For Ungelled IF:

The amodimethicone and the Phat Black DC 9206 dye are added to the Lanol 99 and then mixed using a magnetic bar for 5 min.

The flow rates (in ml/h) used to prepare the compositions 3A and 3B are as follows:

|  | Composition 3A | Composition 3B |
|---|---|---|
| OF | 180 mL/h | 180 mL/h |
| MF | — | 5 mL/h |
| IF | 20 mL/h | 15 mL/h |
| Base | 21.6 mL/h | 21.6 mL/h |

In the manufacture of composition 3A, the IF and the microfluidic device are maintained at 75° C.

The pH and viscosity of compositions 3A (invention) and 3B (comparative) were studied over time, at room temperature and at 50° C. The results are provided in the following tables:

| pH/composition 3A: | | | | | | | | | | | |
|---|---|---|---|---|---|---|---|---|---|---|---|
| T(day) | 1 | 3 | 7 | 14 | 21 | 28 | 56 | 84 | 98 | 112 | 140 | 154 |
| TA | 5.62 | 5.68 | 5.63 | 5.70 | 5.67 | 5.72 | 5.72 | 5.70 | 5.76 | 5.86 | 5.80 | 5.85 |
| 50° C. | 5.76 | 5.47 | 5.56 | 5.76 | 5.71 | 5.72 | 5.63 | 5.65 | 5.67 | 5.77 | 5.70 | 5.75 |

| pH/composition 3B: | | | | | | | | | | | |
|---|---|---|---|---|---|---|---|---|---|---|---|
| T (day) | 1 | 3 | 7 | 14 | 21 | 28 | 56 | 84 | 98 | 126 | 140 | 154 |
| TA | 5.62 | 5.63 | 5.70 | 5.84 | 5.90 | 5.89 | 5.94 | 5.85 | 5.88 | 5.95 | 5.90 | 5.92 |
| 50° C. | 5.52 | 5.72 | 5.77 | 5.79 | 5.84 | 5.82 | 5.75 | 5.70 | 5.74 | 5.82 | 5.83 | 5.80 |

| Viscosity (mPa · s)/composition 3A (10 rpm, 30 sec): | | | | | | | | | | | |
|---|---|---|---|---|---|---|---|---|---|---|---|
| T(day) | 1 | 3 | 7 | 14 | 21 | 28 | 56 | 84 | 98 | 126 | 140 | 154 |
| TA | 10140 | 10360 | 10200 | 10620 | 10560 | 10380 | 10200 | 10000 | 10360 | 10400 | 10500 | 10700 |
| 50° C. | 9000 | 8600 | 8760 | 10940 | 11140 | 10000 | 10140 | 10360 | 10080 | 10180 | 10000 | 10050 |

| Viscosity (mPa · s)/composition 3B (10 rpm, 30 sec): | | | | | | | | | | | |
|---|---|---|---|---|---|---|---|---|---|---|---|
| T(day) | 1 | 3 | 7 | 14 | 21 | 28 | 56 | 84 | 98 | 126 | 140 | 154 |
| TA | 10400 | 10300 | 11060 | 10240 | 10040 | 10220 | 10100 | 10040 | 9680 | 9920 | 9950 | 9980 |
| 50° C. | 9300 | 7940 | 9580 | 10160 | 9460 | 8920 | 9620 | 9930 | 9780 | 9780 | 9780 | 9760 |

In view of these results, it has been shown that the composition 3A according to the invention, comprising a gelled fatty phase, has the same change in pH and viscosity as the comparative composition 3B. Both compositions were found to be advantageously stable over time, whether at room temperature or at a temperature of 50° C.

In addition, regarding the appearance of the drops, no coalescence was observed for the two compositions. Thus, the presence of the gelling agent in the composition 3A does not interact with the aqueous phase and does not disturb the stability of the system.

Example 4

Preparation of a Perfuming Composition

The perfuming composition of Example 4A (perfume serum) according to the invention is a scented product (which may be sprayed) which is stable over time.

Composition 4A is a composition whose drops of fatty phase comprise a gelling agent. It was prepared from the following phase compositions (see table below):

| Composition 4A: | | | |
|---|---|---|---|
| Fluid | Name | INCI | % w/w |
| OF<br>(μ = 552 | Osmosis water | — | 95.036 |
|  | Glycerol | Glycerine | 1.226 |

-continued

| Composition 4A: | | | |
|---|---|---|---|
| Fluid | Name | INCI | % w/w |
| mPa · s | Microcare PTG | Pentyleneglycol | 2.509 |
| pH = 4.60) | Microcare PE | Phenoxyethanol | 0.987 |

-continued

| | Composition 4A: | | |
|---|---|---|---|
| Fluid | Name | INCI | % w/w |
| Base | Carbomer Tego 340 FD | Carbomer | 0.200 |
| | EDETA | Disodium EDTA | 0.040 |
| | NaOH | Sodium hydroxyde | 0.002 |
| | Osmosis water | Water | 99.70 |
| | NaOH | Sodium hydroxyde | 0.30 |
| IF (gelled) | Lanol 99 | Isononyl Isononanoate | 59.50 |
| | Rheopearl KL2 | Dextrin Palmitate | 10.00 |
| | KF 8004 | Amodimethicone | 0.50 |
| | Technobois | Perfumr | 30.00 |

Composition 4B (comparative) is a composition whose drops of fatty phase do not comprise a gelling agent. It was prepared from the following phase compositions (see table below):

| | Composition 4B | | |
|---|---|---|---|
| Fluid | Name | INCI | % w/w |
| OF (μ = 552 mPa · s pH = 4.60) | Osmosis water | — | 95.036 |
| | Glycerol | Glycerine | 1.226 |
| | Microcare PTG | Pentyleneglycol | 2.509 |
| | Microcare PE | Phenoxyehanol | 0.987 |
| | Carbomer Tego 340 FD | Carbomer | 0.200 |
| | EDETA | Disodium EDTA | 0.040 |
| | NaOH | Sodium hydroxyde | 0.002 |
| Base | Osmosis water | Water | 99.70 |
| | NaOH | Sodium hydroxyde | 0.30 |
| IF (not gelled) | Lanol 99 | Isononyl Isononanoate | 58.50 |
| | KF 8004 | Amodimethicone | 0.50 |
| | Technobois | Perfume | 41.00 |
| MF | Lanol 99 | Isononyl Isononanoate | 100 |

Protocol of Preparation

For the OF:
The carbomer is first dispersed in the osmosis water and stirred for 2 hours with a pale deflocculator,
The glycerin is subsequently added. Following these additions, the mixture is stirred for 10 minutes,
Microcare PE, Microcare PTG and EDETA are subsequently added. The mixture is stirred for 5 minutes,
The soda is then added, and
The last step is to mix the solution for 1 hour.

For the Base:
The soda and water are mixed using a magnetic bar for 5 min.

For the Gelled IF:
The Lanol 99 and the perfume are first mixed by magnetic stirring (2 min).
The amodimethicone is added and then mixed using a magnetic bar for 5 min.
The mixture is heated to 80° C. and Rheopearl KL2 is then added with magnetic stirring.
This mixture may then be placed in a water bath heated to 75° C. with magnetic stirring for 1 hour.

For Ungelled IF:
The Lanol 99 and the perfume are first mixed by magnetic stirring (2 min).
The amodimethicone and the Phat Black DC 9206 dye are added and then mixed using a magnetic bar for 5 min.
The flow rates (in mL/h) used to prepare the compositions 4A and 4B are as follows:

| | Composition 4A | Composition 4B |
|---|---|---|
| OF | 150 | 150 |
| MF | — | 4 |
| IF | 16 | 12 |
| Base | 10 | 10 |

In the manufacture of composition 4A, the IF and the microfluidic device are maintained at 75° C.

The pH and the viscosity of the compositions 4A (invention) and 4B (comparative) were studied over time, at room temperature and at 50° C. The results are provided in the following tables:

| pH/composition 4A: | | | | | | | |
|---|---|---|---|---|---|---|---|
| T(days) | 1 | 3 | 7 | 9 | 14 | 21 | 28 |
| TA | 5.99 | 5.51 | 5.48 | 5.51 | 5.55 | 5.46 | 5.58 |
| 50° C. | 4.91 | 5.04 | 5.12 | 5.27 | 5.65 | 5.39 | 5.51 |

| pH/composition 4B: | | | | | | | |
|---|---|---|---|---|---|---|---|
| T(days) | 1 | 3 | 7 | 9 | 14 | 21 | 28 |
| TA | 5.15 | 5.39 | 5.30 | 5.39 | 5.60 | 5.49 | 5.52 |
| 50° C. | 5.53 | 5.39 | 5.31 | 5.36 | 5.52 | 5.38 | 5.35 |

| Viscosity (mPa · s)/composition 4A (10 rpm, 30 sec): | | | | | | | |
|---|---|---|---|---|---|---|---|
| T(days) | 1 | 3 | 7 | 9 | 14 | 21 | 28 |
| TA | 5390 | 3030 | 5850 | 5950 | 5550 | 5380 | 5280 |
| 50° C. | 3680 | 3240 | 6450 | 6180 | 6180 | 6390 | 6400 |

| Viscosity (mPa · s)/Composition 4B (10 rpm, 30 sec): | | | | | | | |
|---|---|---|---|---|---|---|---|
| T(days) | 1 | 3 | 7 | 9 | 14 | 21 | 28 |
| TA | 4180 | 2740 | 5330 | 5180 | 5490 | 5350 | 5180 |
| 50° C. | 4790 | 3030 | 5850 | 5920 | 5790 | 6140 | 6170 |

For perfuming products 4A and 4B, it has been shown that the bubbles are homogeneously distributed in the gel and no coalescence is observed for 3 months.

In conclusion, the products with gelled bubbles and without gelled bubbles have the same stabilities, pH, viscosities and suspensive powers.

Example 5

Preparation of a Gel-Cream Composition With a Dye

The composition of Example 5 is a gel-cream. The composition of Example 5 consists of the following ingredients (see table below):

| Name | INCI name | % w/w PHASES | % w/w |
|---|---|---|---|
| AQUEOUS PHASE GEL | | | |
| Osmosis water | water | SQF * | SQF * |
| Microcare PE | Phenoxyethanol | 0.96 | 0.86 |
| Microcare Emollient PTG | Pentyleneglycol | 2.36 | 2.12 |
| Tego carbomer 340 FD | Carbomer | 0.32 | 0.29 |
| Aristoflex Velvet | Polyacrylate Crosspolymer-11 | 0.086 | 0.077 |
| Rhodicare T | Xanthane | 0.056 | 0.050 |
| Cellosize Hydroxyethyl cellulose PCG-10 | Hydroxyethyl Cellulose | 0.027 | 0.024 |
| Glycerine codex (99%) | Glycerin | 5.89 | 5.27 |
| Zemea | Propanediol | 2.99 | 2.68 |
| Butylene Glycol | Butylene Glycol | 2.95 | 2.64 |
| EDETA BD | Disodium EDTA | 0.039 | 0.035 |
| Sodium Hydroxide Pellets PRS codex | Sodium hydroxide | 0.049 | 0.044 |
| Total | | 100.00 | 89.62 |
| FATTY PHASE | | | |
| DUB ININ | Isononyl Isononanoate | SQF * | SQF * |
| Rheopearl KL2 | Dextrin Palmitate | 15.00 | 1.56 |
| Creasperse White R | Titanium Dioxide, Hydrogenated Polydecene, Hydroxystearic Acid | 0.051 | 0.0053 |
| Phat Blue DC 6204 | CI 61565/CI 60725 | 0.0025 | 0.00026 |
| Nusil CAS 3131 | AmodimEthicone | 0.20 | 0.021 |
| Total | | 100.00 | 10.38 |
| Total | | | 100.00 |

* QSP: sufficient quantity for

The composition of Example 5 is prepared according to the following protocol:

| Outer fluid: OF | | |
|---|---|---|
| NAMD | INCI NAME | % w/w |
| Osmosis water | Water | 84.26 |
| Glycerine codex (99%) | Glycerin | 5.89 |
| Zemea | Propanediol | 2.99 |
| Butylene Glycol | Butylene Glycol | 2.95 |
| Microcare emollient PTG | Pentylenglycol | 2.436 |
| Microcare PE | Phenoxyethanol | 0.96 |
| Tego carbomer 340 FD | Carbomer | 0.32 |
| Aristoflex Velvet | Polyacrylate Crosspolymer-11 | 0.086 |
| Rhodicare T | Xanthane | 0.056 |
| Cellosize Hydroxyethyl cellulose PCG-10 | Hydroxyethyl Cellulose | 0.027 |
| EDETA BD | Disodium EDTA | 0.039 |
| Sodium Hydroxide Pellets PRS codex | Sodium hydroxyde | 0.049 |
| Total | | 100.00 |

| Inter fluid: IF | | |
|---|---|---|
| Name | INCI name | % w/w |
| DUB ININ | Isononyl Isononanoate | SQF * |
| Rheopearl KL2 | Dextrin Palmitate | 15.00 |
| Nusil CAS 3131 | Amodimethicone | 0.20 |
| Creasperse White R | Titanium Dioxide, Hydrogenated Polydecene, Hydroxystearic Acid | 0.051 |
| Phat Blue DC 6204 | CI 61565/CI 60725 | 0.0025 |
| Total | | 100.00 |

| Base: | | |
|---|---|---|
| Name | INCI name | % w/w |
| Osmosis water | Water | SQF * |
| NaOH | Sodium hydroxyde | 2.9929 |
| Total | | 100.00 |

* SQF: sufficient quantity for

Operating Mode of the Phases:

For the OF:

A first phase, called OF1, consists of water and carbomer. This mixture is stirred with a pale deflocculant for 2 hours.

A second phase, called OF 2, is prepared. It consists of glycerin, butylene glycol, Zemea and Rhodicare T. Mixing agitation is performed manually using a spatula for 1 min. The objective is to homogeneously disperse the Rhodicare T powder within the phase.

The OF 2 is added, with stirring, to OF1.

Aristoflex Velvet is added to the mixture using a 1% aqueous solution concentrated in Aristoflex Velvet. In the same way, cellosize hydroxyethyl cellulose PCG-10 is incorporated with an aqueous solution concentrated in Cellosize hydroxyethyl cellulose PCG-10 at 0.5% m. Once these 2 compounds are added, the mixture is stirred for 1 hour.

Microcare PE, Microcare PTG and EDETA are subsequently added. The mixture is stirred for 5 minutes.

Soda is then incorporated.

The last step is to mix the solution for 2 hours.

For the Base:

The soda and water are mixed using a magnetic bar for 5 min.

For the FI:

The amodimethicone is added to the DUB ININ then mixed with a magnetic bar for 15 min.

The mixture is heated to 80° C. and Rheopearl KL2 is then added with magnetic stirring.

Phat Black DC 9206 and Creasperse White R are then added, wherein the resulting mixture is mixed with a magnetic bar for 15 minutes.

This mixture may then be placed in a water bath heated to 85° C. with magnetic stirring for 1 hour.

The flow rates (in mL/h) are as follows:

| | |
|---|---|
| OF | 150 |
| MF | — |
| IF | 20 |
| Base | 2,475 |

During the manufacture of the final composition, the IF and the microfluidic device are maintained at 80° C.

The final composition comprises translucent pale blue dispersed fatty phase drops in a clear, translucent aqueous gel.

Example 6

Preparation of a Hydrating and Anti-Aging Gel-Cream Composition

The composition below is obtained using a "non-microfluidic" method (i.e. by emulsification) as previously described).

| Name | INCI name | % w/w |
|---|---|---|
| Osmosis water | Water | 69.02 |
| Microcare PE | Phenoxyethanol | 0.86 |
| Microcare Emollient PTG | Pentyleneglycol | 2.12 |
| Tego carbomer 340 FD | Carbomer | 0.29 |
| Aristoflex Velvet | Polyacrylate Crosspolymer-11 | 0.077 |
| Rhodicare T | Xanthane | 0.050 |
| Cellosize Hydroxyethyl cellulose PCG-10 | Hydroxyéthyl Cellulose | 0.024 |
| Glycerine codex (99%) | Glycerin | 5.27 |
| Zemea | Propanediol | 2.68 |
| Butylene Glycol | Butylene Glycol | 2.64 |
| EDETA BD | Disodium EDTA | 0.035 |
| Sodium Hydroxide Pellets PRS codex | Sodium gydroxyde | 0.044 |
| DUB ININ | Isononyl Isononanoate | 8.35 |
| Rheopearl KL2 | Dextrin Palmitate | 2.01 |
| OriStar RN | Retinol | 0.5 |
| Vitamin E Acetate | Tocopheryl Acetate | 0.5 |
| Ceramide II | Ceramide NG | 0.5 |
| Nikkol VC-IP | Ascorbyl Tetraisopalmitate | 2 |
| Green Tea Phytolait | Camellia Kissi Seed Oil | 3 |
| Creasperse White R | Titanium Dioxide, Hydrogenated Polydecene, Hydroxystearic Acid | 0.0053 |
| Phat Blue DC 6204 | CI 61565/CI 60725 | 0.00026 |
| Nusil CAS 3131 | Amodiméthicone | 0.021 |
| Total | | 100.00 |

Example 7

Preparation of a Gel-Cream Composition with a Dye

The composition of Example 7 is a gel-cream. The composition of Example 7 consists of the following ingredients (see table below):

| Name | INCI name | % w/w phases | % w/w |
|---|---|---|---|
| AQUEOUS PHASE GEL | | | |
| Osmosis water | Water | SQF * | SQF * |
| Microcare PE | Phenoxyethanol | 0.96 | 0.86 |
| Microcare Emollient PTG | Pentyleneglycol | 2.36 | 2.12 |
| Tego carbomer 340 FD | Carbomer | 0.32 | 0.29 |
| Aristoflex Velvet | Polyacrylate Crosspolymer-11 | 0.086 | 0.077 |
| Rhodicare T | Xanthane | 0.056 | 0.050 |
| Cellosize Hydroxyethyl cellulose PCG-10 | Hydroxyéthyl Cellulose | 0.027 | 0.024 |
| Glycerine codex (99%) | Glycerin | 5.89 | 5.27 |
| Zemea | Propanediol | 2.99 | 2.68 |
| Butylene Glycol | Butylene Glycol | 2.95 | 2.64 |
| EDETA BD | Disodium EDTA | 0.039 | 0.035 |
| Sodium Hydroxide Pellets PRS codex | Sodium hydroxyde | 0.049 | 0.044 |
| Total | | 100.00 | 89.62 |
| FATTY PHASE | | | |
| DUB ININ | Isononyl Isononanoate | SQF * | SQF * |
| Rheopearl MKL2 | Dextrin Myristate | 15 | 2.01 |
| Creasperse White R | Titanium Dioxide, Hydrogenated Polydecene, Hydroxystearic Acid | 0.051 | 0.0053 |
| Phat Blue DC 6204 | CI 61565/CI 60725 | 0.0025 | 0.00026 |
| Nusil CAS 3131 | Amodiméthicone | 0.20 | 0.021 |
| Total | | 100.00 | 10.38 |
| Total | | | 100.00 |

* SQF: sufficient quantity for

The composition of Example 7 is prepared according to a protocol identical to that described in Example 5, with the difference that:
- the Rheopearl KL2 gelling agent is replaced by the Rheopearl MKL2,
- the heating for the preparation of the IF is 90° C., and during the manufacture of the final composition, the IF and the microfluidic device are maintained at 85° C.

The flow rates (in ml/h) are identical to those presented in example 5.

The final composition comprises translucent pale blue dispersed fatty phase drops in a clear, translucent aqueous gel. The dispersed fatty phase of the composition of Example 7 has an improved transparency with respect to that of the composition of Example 5. The Rheopearl MKL2 gelling agent therefore has an advantageous effect in terms of the transparency of the dispersed fatty phase of a composition according to the invention.

Example 8

Preparation of a Gel-Cream Composition

The composition of Example 8 is a gel-cream. The composition of Example 8 consists of the following ingredients (see table below):

| Name | INCI name | % w/w PHASES | % w/w |
|---|---|---|---|
| AQUEOUS PHASE GEL | | | |
| Osmosis water | Water | SQF * | SQF * |
| Microcare PE | Phenoxyethanol | 0.96 | 0.86 |
| Microcare Emollient PTG | Pentyleneglycol | 2.36 | 2.12 |
| Tego carbomer 340 FD | Carbomer | 0.32 | 0.29 |
| Rhodicare T | Xanthane | 0.056 | 0.050 |
| Glycerine codex (99%) | Glycerin | 5.89 | 5.27 |
| Zemea | Propanediol | 2.99 | 2.68 |
| Butylene Glycol | Butylene Glycol | 2.95 | 2.64 |
| EDETA BD | Disodium EDTA | 0.039 | 0.035 |
| Sodium Hydroxide Pellets PRS codex | Sodium hydroxyde | 0.049 | 0.044 |
| Total | | 100.00 | 89.62 |
| FATTY PHASE | | | |
| DUB ININ | Isononyl Isononanoate | SQF * | SQF * |
| Rheopearl KL2 | Dextrin Palmitate | 10.00 | 1.038 |
| Rheopearl MKL2 | Dextrin Myristate | 5.00 | 0.519 |
| Nusil CAS 3131 | Amodimethicone | 0.20 | 0.021 |
| Total | | 100.00 | 10.38 |
| Total | | 100.00 | |

* SQF: sufficient quantity for

The composition of Example 8 is prepared according to a protocol identical to that described in Example 5, with the difference that:
- the IF is devoid of dye and the IF further comprises Rheopearl MKL2 (addition in the IF made simultaneously with the addition of Rheopearl KL2), and
- the preparation of the IF is carried out at 90° C.

The flow rates (in ml/h) are identical to those presented in example 5.

The final composition comprises translucent dispersed fatty phase drops in a clear, translucent aqueous gel. The mixture of gelling agents "Rheopearl KL2/Rheopearl MKL2" is advantageous compared to Rheopearl KL2 alone in that it makes it possible to obtain a fatty phase of improved transparency.

Example 9

Preparation of a Gel-Cream Composition

The composition of Example 9 is a gel-cream. The composition of Example 9 consists of the following ingredients (see table below):

| Name | INCI name | % w/w PHASES | % w/w |
|---|---|---|---|
| AQUEOUS PHASE GEL | | | |
| Osmosis water | Water | SQF * | SQF * |
| Microcare PE | Phenoxyethanol | 0.96 | 0.86 |
| Microcare Emollient PTG | Pentyleneglycol | 2.36 | 2.12 |
| Tego carbomer 340 FD | Carbomer | 0.32 | 0.29 |
| Rhodicare T | Xanthane | 0.056 | 0.050 |
| Glycerine codex (99%) | Glycerin | 5.89 | 5.27 |
| Zemea | Propanediol | 2.99 | 2.68 |
| Butylene Glycol | Butylene Glycol | 2.95 | 2.64 |
| EDETA BD | Disodium EDTA | 0.039 | 0.035 |
| Sodium Hydroxide Pellets PRS codex | Sodium hydroxyde | 0.049 | 0.044 |
| Total | | 100.00 | 89.62 |
| FATTY PHASE | | | |
| DUB ININ | Isononyl Isononanoate | 5 | 0.52 |
| Myritol 318 | Caprylic/Capric Triglyceride | 92.35 | 9.58 |
| Aerosil R202 | silica dimethicone silylate | 2.5 | 0.26 |
| Nusil CAS 3131 | Amodimethicone | 0.15 | 0.015 |
| Total | | 100.00 | 10.38 |
| Total | | 100.00 | |

* SQF: sufficient quantity for

The composition of Example 9 is prepared according to a protocol identical to that described in Example 5, with the difference that:
for the FI:
the amodimethicone is added to the DUB ININ and then mixed with a magnetic bar for 15 minutes,
Myritol 318 is added to the mixture by is understood to mean of magnetic stirring,
the mixture is then placed under mechanical stirring using a pale deflocculator, and
Aerosil R202 is then added to the mixture with stirring that is maintained for 20 min.
all stages of preparation of the phases, in particular the IF, as well as the manufacturing method of the composition are carried out at room temperature.

The flow rates (in ml/h) are identical to those presented in example 5.

The final composition comprises drops of fat phase dispersed in a translucent colorless aqueous gel. The Aerosil R202 gelling agent is advantageous in that it confers on the fatty phase a thixotropic behavior which allows the manufacture of a dispersion according to the invention by implementing a microfluidic method, all the stages of which are carried out ambient temperature.

The invention claimed is:

1. A dispersion containing a dispersed fatty phase comprising drops and a continuous aqueous phase in which the drops comprise a fatty phase containing at least one gelling agent and a shell, wherein the shell comprises at least one anionic polymer and at least one cationic polymer, and wherein said gelling agent is a heat-sensitive gelling agent.

2. The dispersion according to claim 1, wherein the gelling agent is chosen from organic, inorganic, polymeric or molecular lipophilic gelling agents; solid fatty substances at ambient temperature and pressure; and mixtures thereof.

3. The dispersion according to claim 2, wherein the gelling agent is selected from the group consisting of polyacrylates, esters of dextrin and fatty acid(s), glycerol esters of fatty acid(s), polyamides, and mixtures thereof.

4. The dispersion according to claim 3, wherein the esters of dextrin and fatty acid(s) are selected from the group consisting of dextrin palmitates, dextrin myristates, dextrin palmitates/ethylhexanoates, and mixtures thereof.

5. The dispersion according to claim 1, comprising from 0.5% to 99.99% by weight of gelling agent(s) relative to the total weight of the fatty phase.

6. The dispersion according to claim 1, wherein the cationic polymer is a silicone polymer modified with a primary, secondary or tertiary amine function.

7. The dispersion according to claim 1, wherein the cationic polymer has the following formula:

$$R_1 - \left( \begin{array}{c} CH_3 \\ | \\ Si - O \\ | \\ CH_3 \end{array} \right)_x \left( \begin{array}{c} R_2 \\ | \\ Si - O \\ | \\ R_4 \end{array} \right)_y \left( \begin{array}{c} CH_3 \\ | \\ Si \\ | \\ CH_3 \end{array} \right)_z R_3$$

$$\downarrow$$
$$NH_2$$

in which:
$R_1$, $R_2$ and $R_3$, independently of each other, represent OH or $CH_3$;
$R_4$ represents a group —$CH_2$— or a group —X—NH—, in which X is a divalent alkylene radical in $C_3$ or $C_4$;
x is an integer from 10 to 5000;
y is an integer between 2 and 1000; and
z is an integer between 0 and 10.

8. The dispersion according to claim 1, wherein each drop comprises from 0.01% to 10% by weight of cationic polymer(s) relative to the total weight of the fatty phase.

9. The dispersion according to claim 1, wherein the anionic polymer is a polymer comprising monomeric units having at least one carboxylic acid chemical function.

10. The dispersion according claim 1, wherein the dispersion comprises from 0.01% to 5% by weight of anionic polymer(s) relative to the total weight of the dispersion.

11. The dispersion according to claim 1, further comprising at least one biological/cosmetic active agent chosen from hydrating agents, cicatrizing agents, depigmenting agents, UV filters, desquamating agents, antioxidants, active agents stimulating the synthesis of dermal macromeoleculars, active agents stimulating the synthesis of epidermal macromoleculars, dermodecontracting agents, antiperspirants, soothing agents, anti-aging agents, and mixtures thereof.

12. The dispersion according to claim 1, wherein the average diameter of the drops of the dispersed phase is from 0.2 μm to 3000 μm.

13. The dispersion according to claim 1, characterized in that it does not comprise surfactant.

14. The dispersion according to claim 1, comprising at least 5% by weight of glycerin relative to the total weight of the dispersion.

15. The dispersion of claim 1, wherein the continuous aqueous phase is in the form of a gel.

16. A method for preparing the dispersion according to claim 1, comprising the following steps:
optionally heating an oily fluid FI at a temperature of from 40° C. to 150° C.;
contacting an aqueous fluid FE and the oily fluid FI; and
the formation of drops of fatty phase, consisting of the oily fluid FI, dispersed in a continuous aqueous phase, constituted by fluid FE, wherein the drops comprise a shell isolating the core of the drops of the fatty phase of the dispersion,
in which:
the oily fluid FI comprises at least one cationic polymer, and at least one gelling agent, and
the aqueous fluid FE comprises water and at least one anionic polymer.

17. A composition comprising a dispersion according to claim 1, in association with a physiologically acceptable medium.

18. A non-therapeutic method for the cosmetic treatment of a keratin material, comprising a step of applying to the keratin material at least one layer of a cosmetic composition according to claim 17.

19. A non-therapeutic method for the cosmetic treatment of a keratin material, comprising a step of applying to the keratin material a dispersion according to claim 1.

* * * * *